US007821409B2

(12) United States Patent  
Ishida

(10) Patent No.: US 7,821,409 B2  
(45) Date of Patent: Oct. 26, 2010

(54) DROWSINESS ALARM APPARATUS AND PROGRAM

(75) Inventor: Kenji Ishida, Nagoya (JP)

(73) Assignee: DENSO CORPORATION, Kariya (JP)

( * ) Notice: Subject to any disclaimer, the term of this patent is extended or adjusted under 35 U.S.C. 154(b) by 325 days.

(21) Appl. No.: 12/076,873

(22) Filed: Mar. 25, 2008

(65) Prior Publication Data

US 2008/0238694 A1    Oct. 2, 2008

(30) Foreign Application Priority Data

Mar. 26, 2007    (JP)    ............................ 2007-079310

(51) Int. Cl.
*G08B 23/00* (2006.01)
(52) U.S. Cl. ........................ 340/576; 340/439; 340/575; 382/118
(58) Field of Classification Search ...... 340/573.1–576, 340/439, 5.83, 539.12; 701/1, 41; 382/104, 382/118

See application file for complete search history.

(56) References Cited

U.S. PATENT DOCUMENTS

| 5,878,156 | A | * | 3/1999 | Okumura | ..................... 382/118 |
| 6,130,617 | A | * | 10/2000 | Yeo | ............................ 340/575 |
| 7,692,551 | B2 | * | 4/2010 | Bonefas et al. | ............... 340/575 |
| 2003/0201895 | A1 | * | 10/2003 | Harter et al. | ................. 340/575 |
| 2005/0024212 | A1 | * | 2/2005 | Hultzsch | ..................... 340/575 |

FOREIGN PATENT DOCUMENTS

| JP | A-05-060515 | 3/1993 |
| JP | A-06-076058 | 3/1994 |
| JP | A-06-348980 | 12/1994 |
| JP | A-07-032995 | 2/1995 |
| JP | A-07-181012 | 7/1995 |
| JP | A-08-294694 | 11/1996 |
| JP | A-09-198508 | 7/1997 |
| JP | A-09-270010 | 10/1997 |
| JP | A-11-066304 | 3/1999 |
| JP | A-2000-172966 | 6/2000 |
| JP | A-2000-198369 | 7/2000 |

(Continued)

OTHER PUBLICATIONS

Office Action dated Jan. 26, 2009 in corresponding Japanese patent application No. 2007-079310 (and English translation).

*Primary Examiner*—Brent Swarthout
(74) *Attorney, Agent, or Firm*—Posz Law Group, PLC

(57) ABSTRACT

A drowsiness alarm apparatus and a program for decreasing the possibility of incorrectly issuing an alarm due to an expressed emotion is provided. A wakefulness degree calculation apparatus performs a wakeful face feature collection process to collect a wakefulness degree criterion and an average representative feature distance. A doze alarm process collects a characteristic opening degree value and a characteristic feature distance. The wakefulness degree criterion is compared with the characteristic opening degree value to estimate a wakefulness degree. The average representative feature distance is compared with the characteristic feature distance to determine whether the face of the driver expresses a specific emotion. If the face expresses the emotion, alarm output is inhibited. When the face does not express the emotion, an alarm is output in accordance with the degree of decreased wakefulness so as to provide an increased alarm degree for the driver if necessary.

21 Claims, 14 Drawing Sheets

FOREIGN PATENT DOCUMENTS

| | | |
|---|---|---|
| JP | A-2001-043345 | 2/2001 |
| JP | A-2004-192551 | 7/2004 |
| JP | A-2005-028916 | 2/2005 |
| JP | A-2005-251224 | 9/2005 |
| JP | A-2006-123136 | 5/2006 |
| JP | A-2007-106337 | 4/2007 |
| JP | A-2007-106360 | 4/2007 |

* cited by examiner

DROWSINESS ALARM APPARATUS AND PROGRAM

CROSS REFERENCE TO RELATED APPLICATIONS

The present invention is based on and claims priority to Japanese Patent Application No. 2007-79310 filed on Mar. 26, 2007 the entire contents of which are incorporated herein by reference.

BACKGROUND OF THE INVENTION

1. Field of the Invention

The present invention relates to a drowsiness alarm apparatus and, more specifically to an alarm apparatus and program for reducing the possibility of an incorrectly issued alarm.

2. Description of the Related Art

A conventional drowsiness alarm apparatus including a photographic means, a wakefulness estimate means, and an alarm means is known. The photographic means sequentially photographs a driver's face. The wakefulness estimate means processes an image photographed, acquired, or otherwise captured by the photographic means and estimates the wakefulness degree of the driver. The alarm means generates an alarm assuming that the driver feels drowsy when the wakefulness estimate means estimates a wakefulness degree to be low.

Such a drowsiness alarm apparatus sequentially calculates an opening degree of an eye of the driver based on the photographed image and, for example, on a distance between upper and lower eyelids, which can be referred to hereinafter as an opening degree value, obtained from the image. The apparatus accumulates the calculated opening degree values at a predetermined time interval and calculates an accumulated value. When the accumulated value is less than or equal to a specified value, the apparatus determines the wakefulness state to be low as described for example, in JP-1995-181012A.

Disadvantages become apparent with such as system however in that a driver who expresses emotions while driving a vehicle may change the degree of eye opening. Depending on the emotion, the opening degree value may become smaller than the normal opening degree value that is present when the wakefulness degree is high and no emotion is expressed. For example, a smile will tend to narrow the eye opening and decrease the opening degree value. In such a situation, a conventional drowsiness alarm apparatus may incorrectly assume the driver to be drowsy and issue an alarm simply because the emotion is expressed.

SUMMARY OF THE INVENTION

It is therefore an object of the invention to provide a drowsiness alarm apparatus and a program for decreasing the possibility of incorrectly issuing an alarm due to an expressed emotion.

In a drowsiness alarm apparatus according to various exemplary embodiments for achieving the above-mentioned object, an image acquisition means acquires or otherwise captures a facial image of an occupant in a vehicle such as the driver of the vehicle. Based on the captured facial image acquired by the image acquisition means, a wakefulness estimate means detects an estimated index predetermined as an index for estimating a wakefulness degree of the occupant. Based on the detected estimated index, the wakefulness estimate means generates an estimated wakefulness degree indicating a wakefulness degree of the occupant. An alarm means performs an alarm process for issuing an alarm when an estimated wakefulness degree generated by wakefulness estimate means is smaller than a predetermined prescriptive wakefulness degree. A specific emotion determination means determines a specific emotion out of facial emotions based on a change in the estimated index for the specific emotion that indicates a tendency similar to a decrease in the wakefulness degree. Based on a predetermined emotion index extracted from the captured image, the specific emotion determination means determines whether a face in the captured image expresses the specific emotion. When it is determined that a specific emotion is expressed, an inhibition means inhibits the alarm means from performing an alarm process.

The drowsiness alarm apparatus according to various exemplary embodiments inhibits the alarm process from being performed when the specific emotion is determined to be expressed. The drowsiness alarm apparatus can decrease the possibility of incorrectly issuing an alarm even when the specific emotion is only slightly expressed on the face. The drowsiness alarm apparatus can further solve the problem that the wakefulness estimate means incorrectly estimates a wakefulness degree to be lower than that actually felt by an occupant. In such a situation drowsiness is incorrectly recognized when the occupant feels no drowsiness. As a result, the drowsiness alarm apparatus can prevent the occupant from experiencing inconvenience associated with the incorrect alarm.

When the alarm means inhibits the alarm process from being performed, it may be preferable to inhibit the wakefulness estimate means from generating the estimated wakefulness degree or only inhibit an alarm from being output.

In a drowsiness alarm apparatus according to various exemplary embodiments, an image acquisition means acquires or otherwise captures a facial image of an occupant in a vehicle. Based on the captured image acquired by the image acquisition means, a first estimated index detection means detects a first estimated index predetermined for estimating the wakefulness degree of the occupant. A second estimated index detection means detects a second estimated index that differs from the first estimated index and is predetermined for estimating the wakefulness degree of the occupant. A wakefulness estimate means generates an estimated wakefulness degree indicating the wakefulness degree of the occupant based on the first or second estimated index. An alarm means performs an alarm process for issuing an alarm when an estimated wakefulness degree generated by the wakefulness estimate means is smaller than a predetermined prescriptive wakefulness degree.

A specific emotion determination means determines a specific emotion out of facial emotions based on a change in the first estimated index for the specific emotion indicating a tendency similar to a decrease in the wakefulness degree. Based on a predetermined emotion index extracted from the captured image, the specific emotion determination means determines whether a face in the captured image expresses the specific emotion. A switchover means may switch between the following cases. In one case, the wakefulness estimate means generates the estimated wakefulness degree based on a first estimated index when the specific emotion determination means determines no expression of a specific emotion. In the other case, the wakefulness estimate means generates the estimated wakefulness degree based on a second estimated index when the specific emotion determination means determines expression of a specific emotion.

The drowsiness alarm apparatus constructed as mentioned above can reduce the possibility of incorrectly issuing an alarm according to the wakefulness degree assumed to be low simply because the specific emotion is expressed.

The drowsiness alarm apparatus according to various exemplary embodiments generates an estimated wakefulness degree based on the second estimated index when the specific emotion is determined to be expressed. The drowsiness alarm apparatus performs the alarm process when the estimated wakefulness degree is smaller than the prescriptive wakefulness degree. An alarm can be issued when an occupant is more likely to actually feel drowsy.

The first estimated index signifies an eye opening degree such as a distance between upper and lower eyelids. The second estimated index is independent of the first estimated index and signifies degrees of a slacked mouth, a raised eyebrow, and a tilted head.

In the following description, an emotion expression determination signifies a process of determining whether an emotion is expressed based on a captured image. As a general example of the emotion expression determination, templates for emotions are previously stored in memory. A captured image is compared to the templates. When they match at a predetermined rate or higher, such as by way of a degree of correlation between predetermined feature points in the image, the emotion is assumed to be expressed.

An apparatus for processing the emotion expression determination uses templates corresponding to images of emotions expressed on the face. It will be appreciated that a number of templates to be stored in the memory should correspond to the number of different emotions and variations of each individual emotion to be detected. The memory requires a large capacity. In addition, since the captured image is compared to all the templates, a process for the emotion expression determination can become overloaded.

To solve this problem, the specific emotion determination means in the drowsiness alarm apparatus according to various exemplary embodiments is constructed. The feature distance calculation means extracts one or more pairs of feature points from a captured image. The pair of feature points is defined as having varied distance therebetween in connection with a specific muscle, such as a facial muscle showing different contraction states depending on expression of the specific emotion and a decrease in the wakefulness degree. The feature distance calculation means calculates a feature angle between extracted feature points or a feature distance between the feature points. The feature angle or the feature distance is used as the emotion index.

According to the above-mentioned construction, the drowsiness alarm apparatus of the invention can acquire the emotion index and determine expression of the specific emotion simply by detecting feature points and calculating a distance or an angle between the feature points. There is no need to store templates used for the emotion expression determination in the memory. The memory capacity can be reduced. The emotion expression determination according to the above-mentioned construction eliminates the need for comparison between the templates and a captured image, making it possible to lighten the process.

According to available scientific knowledge, a corrugator muscle, known, for example, as the musculus corrugator supercili, is a small, narrow, pyramidal muscle, placed at the medial end of the eyebrow, beneath the frontalis and orbicularis oculi. The corrugator muscle is known to contract when the face expresses specific emotions such as uneasiness, anger, sadness, disgust, and surprise. The corrugator muscle does not contract when a wakefulness degree is low.

When the drowsiness alarm apparatus according to various exemplary embodiments assumes the corrugator muscle to be the specific muscle as described above, the feature points in the drowsiness alarm apparatus include a feature pair including an inner end of a left eyebrow and an inner corner of a right eye, or can include a feature pair including an inner end of a right eyebrow and an inner corner of a left eye. That is, the drowsiness alarm apparatus of the invention uses a distance between the inner end of left eyebrow and the inner corner of right eye or a distance between the inner corner of left eye and the inner end of right eyebrow as the feature distance. The drowsiness alarm apparatus may estimate a contraction of the corrugator muscle or that a specific emotion is expressed when the feature distance becomes shorter than a normal state, such as a wakefulness state having no specific emotion expressed.

According to available scientific knowledge, an elevator muscle of the upper eyelid, known, for example, as the musculus levator (lavator) palpebrae superoris contracts when the face expresses specific emotions such as surprise, joy, uneasiness, and anger. The levator palpebrae superioris loosens when a wakefulness degree is low.

When the drowsiness alarm apparatus according to various exemplary embodiments may assume the levator palpebrae superioris to be the specific muscle as described above, the feature points in the drowsiness alarm apparatus of the invention may calculate feature distances based on an upper eyelid top, an inner corner of eye, and an outer corner of eye. The drowsiness alarm apparatus may estimate the levator palpebrae superioris to contract or the specific emotion to be expressed when the feature distance becomes shorter than the normal state. In particular, the feature distance can be a distance between the upper eyelid top and at least one of the inner corner of eye and the outer corner of eye in a height direction.

According to available scientific knowledge, both a greater zygomatic muscle known as, for example, musculus zygomaticus major, and a laughing muscle, known as for example, musculus risorius, and other muscles contract when the face expresses a specific emotion such as joy. The greater zygomatic muscle and the risorius muscle do not contract when a wakefulness degree is low. The greater zygomatic muscle and the risorius muscle contract when the face expresses a specific emotion such as joy. The greater zygomatic muscle and the risorius muscle loosen when a wakefulness degree is low.

Accordingly, when the drowsiness alarm apparatus according to various exemplary embodiments assumes at least one of the greater zygomatic muscle and the risorius muscle to be the specific muscle as described above, the feature points in the drowsiness alarm apparatus of the invention preferably include the inner corner of eye and a mouth corner. That is, the drowsiness alarm apparatus of the invention may calculate feature distances based on the inner corner of eye and the mouth corner. The drowsiness alarm apparatus may estimate at least one of the greater zygomatic muscle and the risorius muscle to contract or the specific emotion to be expressed when the feature distance becomes shorter than the normal state. The feature distance may indicate a distance between the inner corner of eye and the mouth corner in a horizontal direction such as a shoulder width direction or a distance between the inner corner of eye and the mouth corner in a vertical direction such as a height direction.

When the greater zygomatic muscle is assumed to be the specific muscle, the feature points in the drowsiness alarm apparatus include the mouth corner and a tragus point. The drowsiness alarm apparatus of the invention uses the feature distance equivalent to a distance between the mouth corner and the tragus point. The drowsiness alarm apparatus may estimate the greater zygomatic muscle to contract or the specific emotion to be expressed when the feature distance becomes shorter than the normal state.

In an exemplary drowsiness alarm apparatus, the feature distance calculation means may extract the feature point and calculate the feature distance for left and right parts of the face independently of each other. The specific emotion determination means may assign the emotion index to one of left and right feature distances independently calculated by the feature distance calculation means based on the feature distance indicating a large variation.

The drowsiness alarm apparatus according to an exemplary construction associates an emotion index with the feature distance for the left part of the face or for the right part of the face whichever shows a large variation. It is thereby possible to more accurately determine whether the face expresses the specific emotion. Further, a specific emotion that is expressed by an occupant in a more pronounced manner on one side of the face as compared to the other, can be more reliably determined.

When the corrugator muscle is assumed to be the specific muscle, the feature points in the drowsiness alarm apparatus can include inner ends of left and right eyebrows. The drowsiness alarm apparatus of the invention uses the feature distance equivalent to a distance between the inner ends of left and right eyebrows. The drowsiness alarm apparatus may estimate the corrugator muscle to contract or the specific emotion to be expressed when the feature distance becomes shorter than the normal state.

It should be noted that in some embodiments, the invention may be provided as a program such as a computer program provided as a product or other article of manufacture including a computer readable medium. The medium can include a recording medium such as an optical or magnetic recording medium, or other recording medium, such as a DVD-ROM, CD-ROM, or a hard disk, and can include a communication medium such as an information carrier propagating on a wired or wireless communication channel. Instructions can be provided on the medium, which, when read and executed can cause a computer, processor or the like to perform certain useful procedures and provide useful results in accordance with the exemplary embodiments described herein.

BRIEF DESCRIPTION OF THE DRAWINGS

Other objects, features and characteristics of the present invention will be appreciated and become apparent to those of ordinary skill in the art and all of which form a part of the present application. In the drawings.

DETAILED DESCRIPTION OF THE EXEMPLARY EMBODIMENTS

Embodiments of the present invention will be described in further detail with reference to the accompanying drawings.

Figure 1:
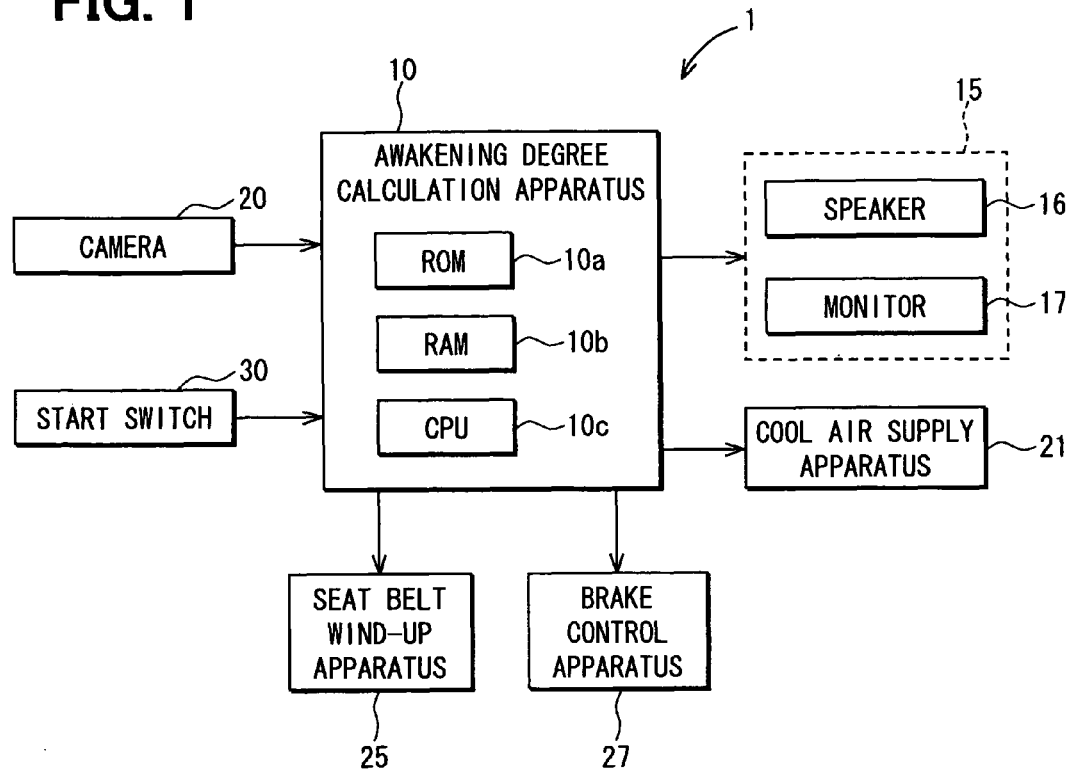
FIG. 1 a block diagram illustrating an exemplary construction of a drowsiness alarm system.
Figure 2:
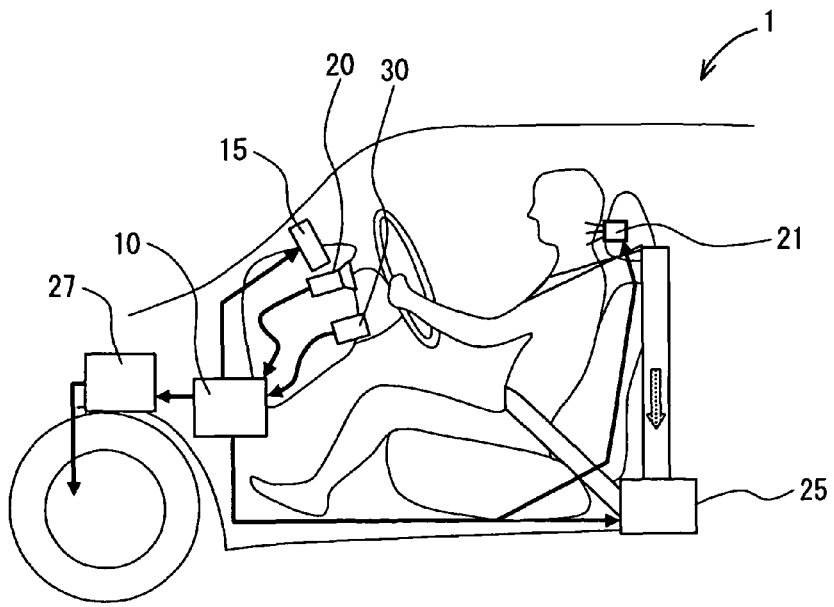
FIG. 2 is a diagram illustrating an exemplary drowsiness alarm system mounted inside of a vehicle mounted.

A vehicle mounted with the drowsiness alarm system for example as shown in FIG. 1 and FIG. 2 can be referred to as a system-mounted vehicle. According to various exemplary embodiments of the system-mounted vehicle, a drowsiness alarm system 1 includes a camera 20, an alarm apparatus 15, a cool air supply apparatus 21, a seat belt wind-up apparatus 25, a brake control apparatus 27, a wakefulness degree calculation apparatus 10, and a start switch 30. The camera 20 is installed in an instrument panel so as to direct a lens toward a driver seat in a vehicle compartment so as to be positioned to capture a specified area including a face of the driver. The alarm apparatus 15 is installed on the instrument panel and generates an alarm. The cool air supply apparatus 21 is installed in a head resting of the driver seat and supplies cool air to the driver. The seat belt wind-up apparatus 25 winds up a set belt of the driver seat. The brake control apparatus 27 controls a braking force of the brake. The wakefulness degree calculation apparatus 10 calculates a wakefulness degree of the driver based on an image captured by the camera 20 and controls the alarm apparatus 15, the cool air supply apparatus 21, the seat belt wind-up apparatus 25, and the brake control apparatus 27 in accordance with the calculated wakefulness degree. The start switch 30 supplies a start signal for starting the drowsiness alarm system 1.

The camera 20 uses a charge coupled device (CCD) or a complimentary metal oxide semiconductor (CMOS) including an imaging element and an image processing engine. The imaging element converts an intensity of light received through a lens into an electric signal or series of electrical signals such as through an array of light sensitive elements that are periodically scanned. The image processing engine converts the electric signal from the imaging element into a digital signal and generates a digital image containing image data based on the digital signal. It will be appreciated that the image data may be referred to as an image frame. The camera 20 generates the image frame of image data from the imaging element at a predetermined time interval, such as one frame every 1/30 s and captures a specified area including the face of the driver to generate a stream of digital image frames. It should be noted that in the following description, a digital image generated by the image processing engine can be referred to as a captured image.

The alarm apparatus 15 includes a speaker 16 and a monitor 17. The speaker 16 sounds in accordance with an audio signal output from the wakefulness degree calculation apparatus 10. The monitor 17 displays an image in accordance with a video signal output from the wakefulness degree calculation apparatus 10. To provide a better view for the driver, the monitor 17 is installed on the instrument panel.

The cool air supply apparatus 21 uses a known technology for applying cool or warm air to a person sitting on the seat. The wakefulness degree calculation apparatus 10 transmits a control instruction for supplying cool air or warm air, whereupon the air supply apparatus 21 applies the air to the neck of the driver.

In response to the transmission of a control instruction from the wakefulness degree calculation apparatus 10, the seat belt wind-up apparatus 25 winds up the seat belt on the drivers seat to increase a binding force of the seat belt.

In accordance with a control instruction from the wakefulness degree calculation apparatus 10, the brake control apparatus 27 controls a brake actuator that opens and closes a pressure boost valve and a pressure reducing valve provided for a brake hydraulic control circuit.

The wakefulness degree calculation apparatus mainly includes a known microcomputer having at least ROM 10a, RAM 10b, and a CPU 10c. The ROM 10a stores processing programs. The RAM 10b temporarily stores data. The CPU 10c performs various processes in accordance with a processing program stored in the ROM 10a or the RAM 10b.

The ROM 10a of the wakefulness degree calculation apparatus 10 stores the processing programs for performing a wakeful face feature collection process and a doze alarm process. Based on a captured image associated with wakefulness, the wakeful face feature collection process collects facial features of the driver associated with wakefulness, which can be referred to as a reference feature value. Based on a captured image associated with driving, the doze alarm process collects facial features of the driver that are associated with the present driving condition of the driver, which can be referred to as a driving feature value. The doze alarm process compares the driving feature value with the reference feature value and transmits a control instruction when there is a decrease in wakefulness without an expression of emotion or other non wakefulness-related movement of the feature points.

Specifically, the wakefulness degree calculation apparatus 10 performs the wakeful face feature collection process to collect the reference feature value and then performs the doze alarm process to collect a driving feature quantity. The wakefulness degree calculation apparatus 10 compares the reference feature value with the driving feature value to check the wakefulness degree of the driver and determine whether the face of the driver shows any emotion. When it is determined that the wakefulness degree of the driver decreases and the expression of the driver shows no emotion, the wakefulness degree calculation apparatus 10 transmits various control instructions to the alarm apparatus 15.

Figure 6:
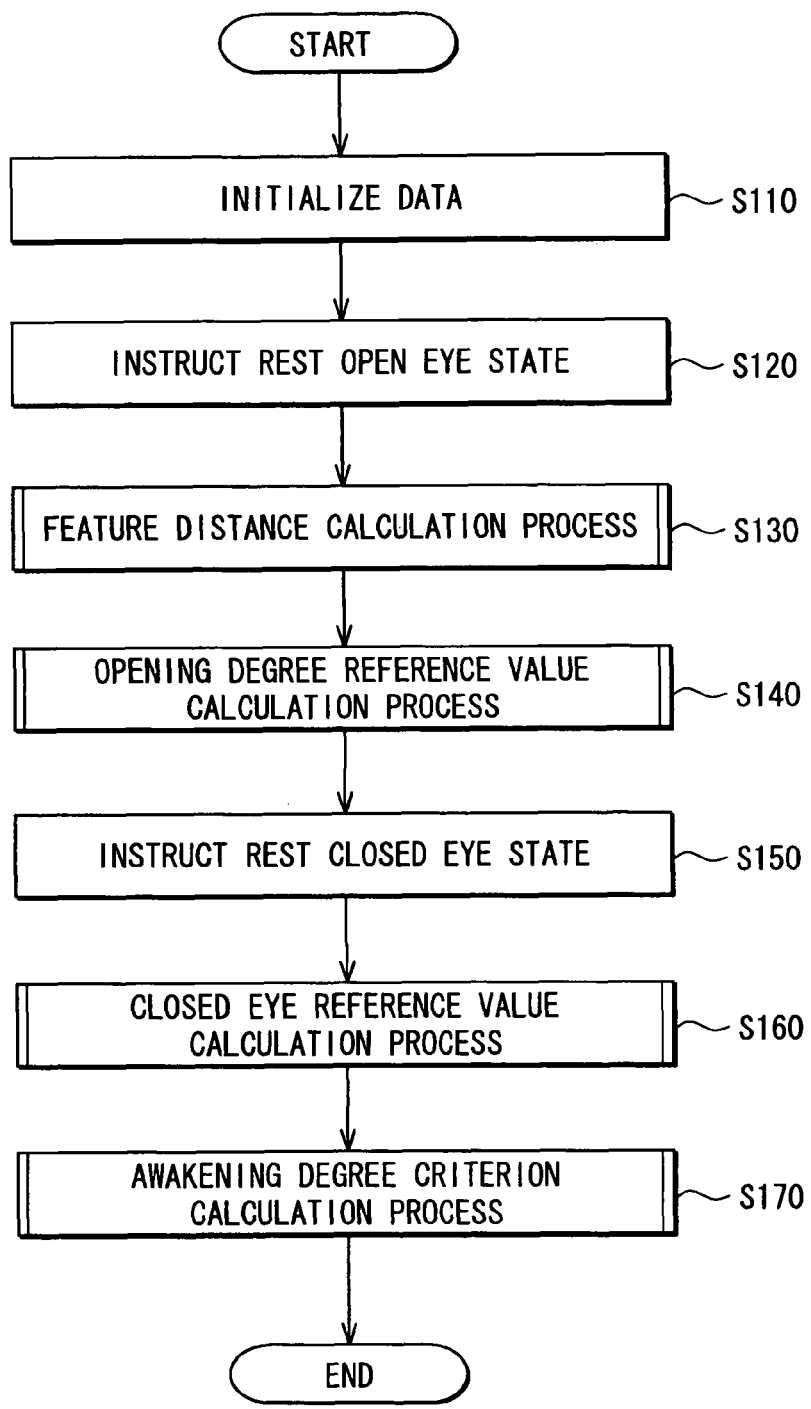
FIG. 6 is a flowchart illustrating portions of an exemplary wakeful face feature collection process.

The wakeful face feature collection process, as shown in FIG. 6, can be performed by the CPU 10c and starts, for example, when a start instruction is input such as when the start switch 30 is turned on. As shown in FIG. 6, the process starts by, for example, initializing data at S110. Specifically, according to the present embodiment, the process deletes captured images and reference feature values, such as a representative feature distance and an average representative opening degree value to be described in greater detail hereinafter, that are stored in the RAM 10b from a previous driving session.

At S120, the process outputs a speech segment from the speaker 16 that instructs the driver, for example, to "look at the point of gaze" and displays an appropriate image on the monitor 17. The objective of S120 is to momentarily maintain and capture a quiescent or resting open eye state, such as a state in which the driver looks at the point of gaze to be focused on during the driving.

At S130, a feature distance calculation process is performed. The camera 20 captures a sequence of images including the face of the driver in the resting open eye state. Based on the captured images, the feature distance calculation process calculates a feature distance between predetermined feature points on the face portion of the captured image.

At S140, an opening degree reference value calculation process is performed. The camera 20 captures a sequence of images including the face of the driver in the resting open eye state. Based on the captured images in the resting open eye state as mentioned above, the opening degree reference value calculation process calculates an opening degree value, such as an opening degree of the eyes of the driver in the resting open eye state represented by a distance between upper and lower eyelids.

At S150, the process outputs a speech segment from the speaker 16 that instructs the driver, for example, to "close your eyes" and displays an appropriate image on the monitor 17. The objective of S150 is to momentarily maintain and capture a quiescent or resting closed eye state, based on the driver closing their eyes by keeping their face at the same position, for example, as that in the resting open eye state.

At S160, the process then performs a closed eye reference value calculation process. The camera 20 captures a sequence of images including the face of the driver in the resting closed eye state. Based on the captured images, the closed eye reference value calculation process calculates a closed eye value, such as an opening degree value of the driver in the resting closed eye state.

At S170, a wakefulness degree criterion calculation process is performed. The wakefulness degree criterion calculation process calculates a wakefulness degree criterion that can be used to estimate or judge the wakefulness degree of the driver during driving based on the opening degree value calculated at S140 and the closed eye value calculated at S160. The wakeful face feature collection process then terminates. However it will be appreciated that in a driving session, the wakefulness degree criterion calculation process can be repeated periodically so as to amount to continuous monitoring. It should be noted that the wakeful face feature collection process prepares the wakefulness degree criteria, which is used to estimate a wakefulness degree of the driver in connection with the doze alarm process.

Figure 7:
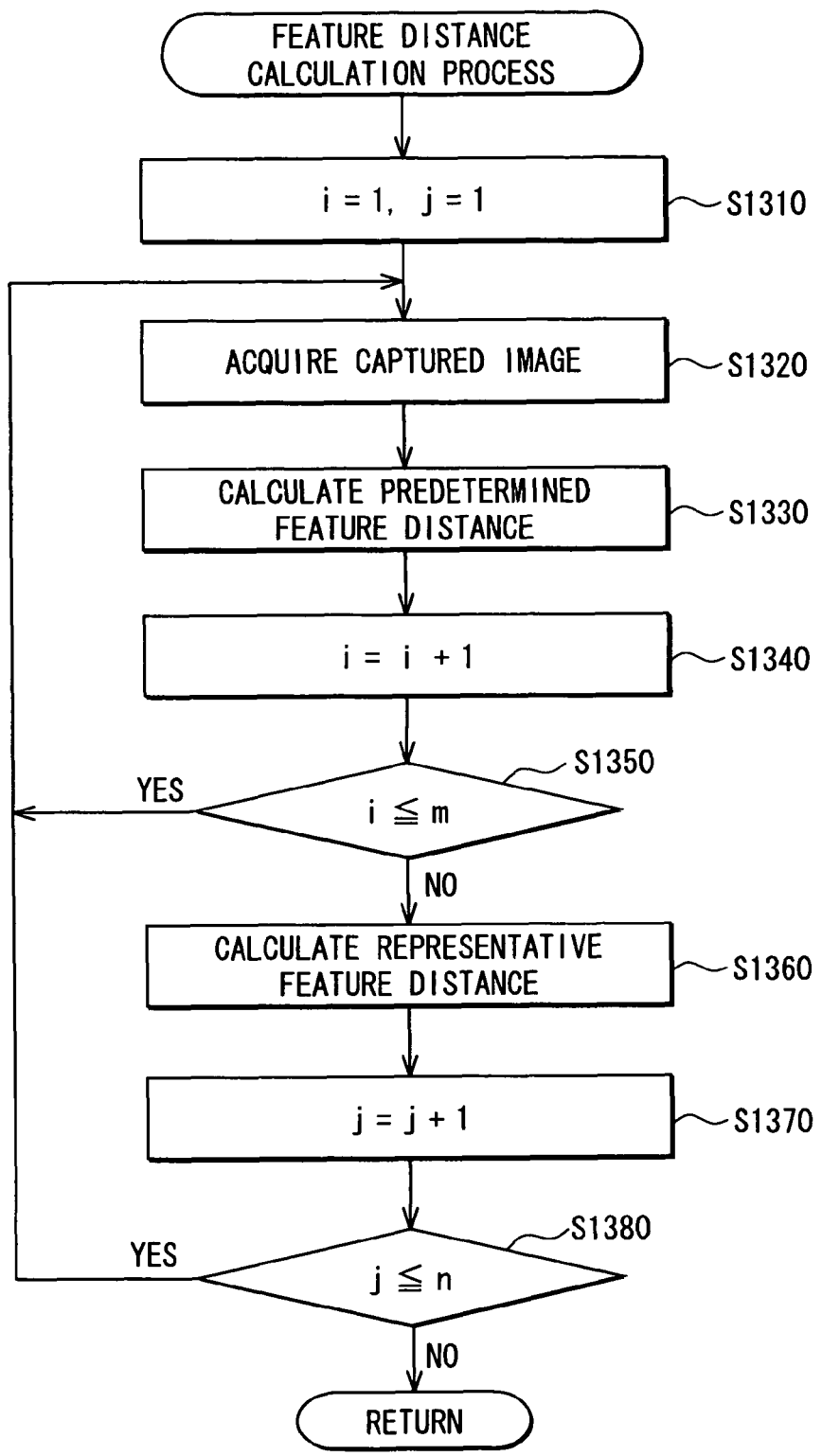
FIG. 7 is a flowchart illustrating portions of an exemplary feature distance calculation process.

The feature distance calculation process shown and described in connection with FIG. 7 is performed in the wakeful face feature collection process and starts at S130. At S1310, the process sets a first counter such as "i" and a second counter such as "j" to initial values such as 1 s according to the present embodiment. At S1320, the process acquires a captured image from the camera 20. At S1330, the captured image is processed and the multiple predetermined feature points are extracted. Based on the extracted feature points, the process calculates a predetermined feature distance.

Specifically, the system according to the embodiment first digitizes a captured image. From the digitized captured image, the system extracts a feature point by detecting an edge, such as a boundary between white and black image areas. The system acquires a position such as a Cartesian coordinate, or (x, y) position of the feature point. The technology for extracting feature points is known as disclosed, for example, in JP-B No. 101904/1995 and a detailed description is omitted for simplicity.

Figure 3:
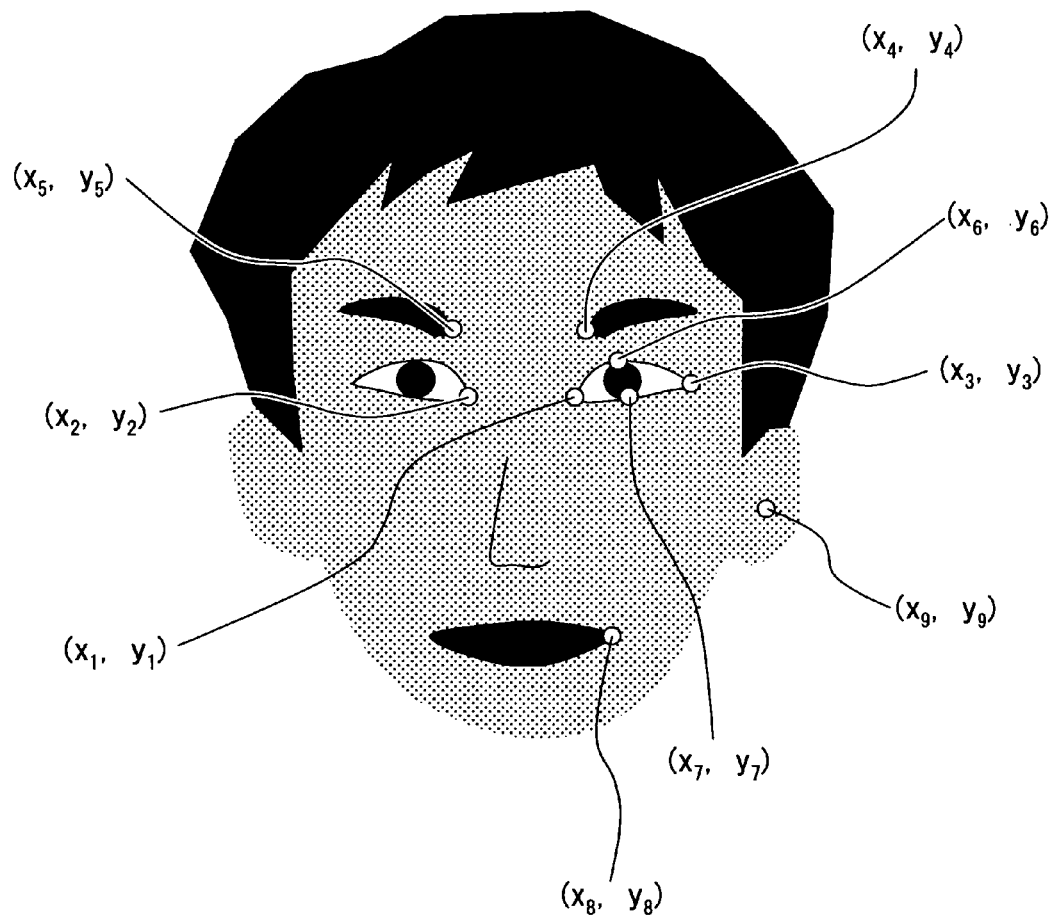
FIG. 3 is a diagram illustrating feature points in accordance with various exemplary embodiments.

As shown in FIG. 3, the feature points include an inner corner of left eye at coordinates (x1, y1), an outer corner of right eye at (x2, y2), an outer corner of eye at (x3, y3), an upper eyelid top at (x6, y6) such as a boundary between an eyelid and part of an eyeball nearest to the parietal region, an inner end of left eyebrow at (x4, y4), an inner end of right eyebrow at (x5, y5), a mouth corner at (x8, y8), and a tragus point at (x9, y9). Similarly to the inner corner of eye and the inner end of eyebrow, the outer corner of eye, the upper eyelid top, the mouth corner, and the tragus point are extracted from the left and right sides of the face.

Based on the acquired feature point positions, the system then calculates a prescriptive distance on the left and right sides of the face. The system divides the prescriptive distance by a distance between the inner corners of both eyes to calculate the feature distance.

Figure 4A:
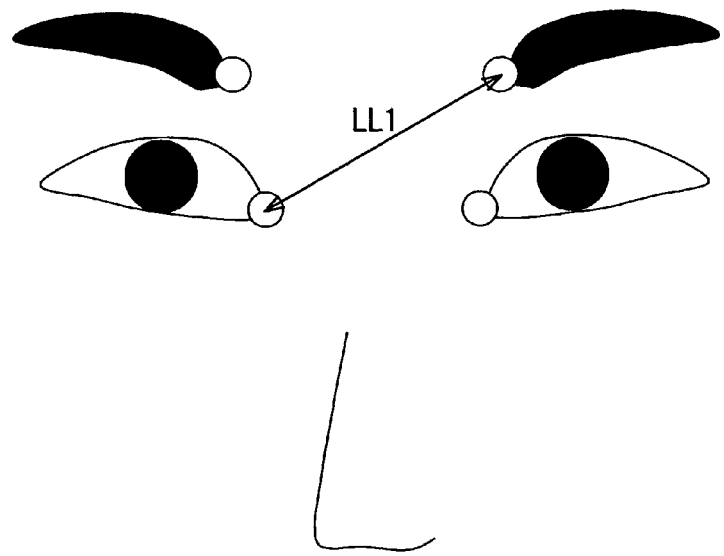
FIG. 4A is a diagram illustrating exemplary feature distances.
Figure 4B:
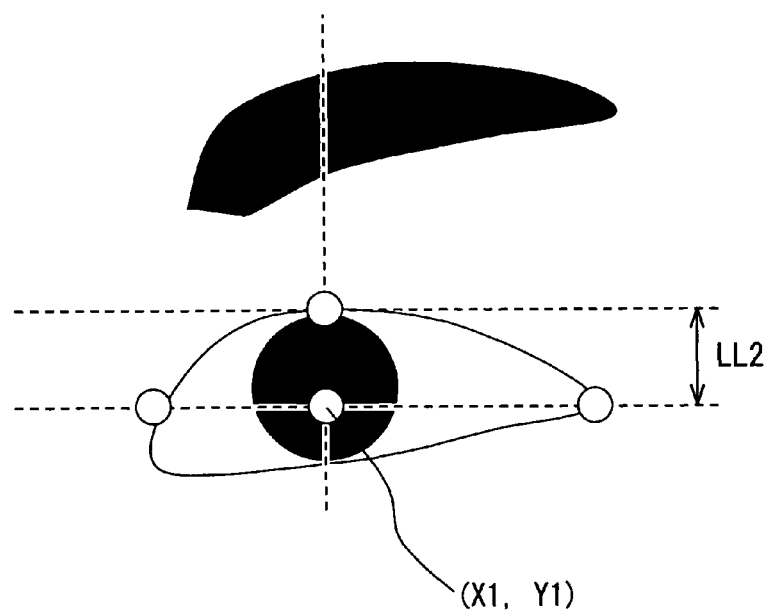
FIG. 4B is a diagram further illustrating exemplary feature distances.
Figure 5:
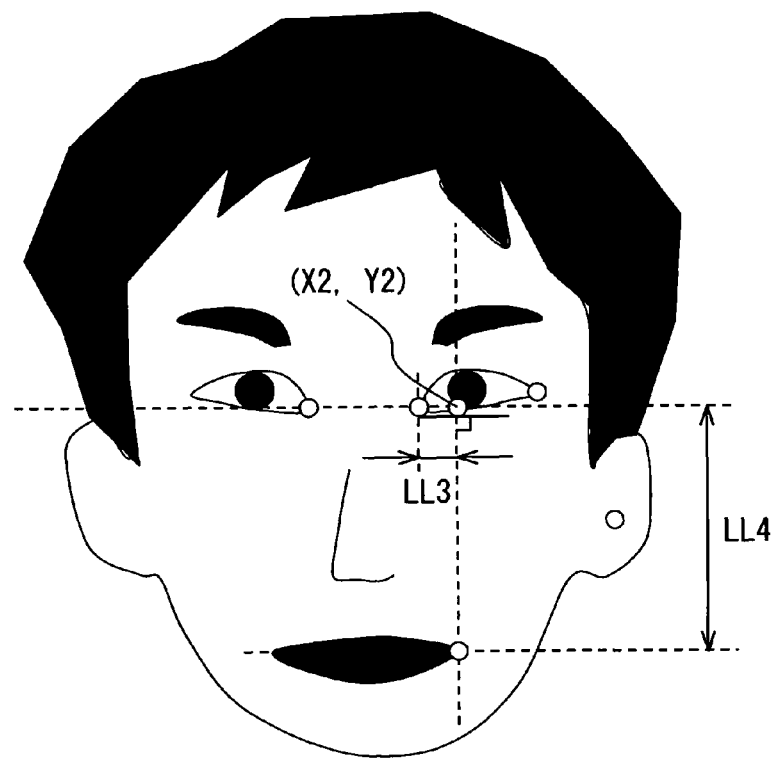
FIG. 5 is a diagram still further illustrating exemplary feature distances.

The prescriptive distances include a first prescriptive distance LL1 as shown in FIG. 4A and a second prescriptive distance LL2 as shown in FIG. 4B. The first prescriptive distance LL1 indicates a distance between the inner corner of eye and the inner end of eyebrow. The second prescriptive distance LL2 indicates a distance between the upper eyelid top and an intersection point at (X1, Y1) between a first reference line and a perpendicular line from the upper eyelid top. The first reference line connects the inner corner of eye with the outer corner of eye. FIG. 5 shows a third prescriptive distance LL3 and a fourth prescriptive distance LL4. The third prescriptive distance LL3 indicates a distance between the inner corner of eye and an intersection point at (X2, Y2) between a second reference line connecting the inner corners of both eyes with a perpendicular line from the mouth corner. That is, the third prescriptive distance LL3 indicates a distance between the inner corner of eye and the mouth corner in a shoulder width direction. The fourth prescriptive distance LL4 indicates a distance between the mouth corner and an intersection point at (X2, Y2) between the second reference line and a perpendicular line from the mouth corner. That is, the fourth prescriptive distance LL4 indicates a distance between the inner corner of eye and the mouth corner in a height direction. These prescriptive distances vary in interlock with at least one of a corrugator muscle, an levator palpebrae superioris, a greater zygomatic muscle, and a risorius muscle.

Equation (1) is used to calculate the first feature distance L1. Equation (2) is used to calculate the second feature distance L2. Equation (3) is used to calculate the third feature distance L3. Equation (4) is used to calculate the fourth feature distance L4.

$$L1 = \frac{\sqrt{(x4-x2)^2 + (y4-y2)^2}}{\sqrt{(x1-x2)^2 + (y1-y2)^2}} \quad (1)$$

$$L2 = \frac{\sqrt{(x6-x1)^2 + (y6-Y1)^2}}{\sqrt{(x1-x2)^2 + (y1-y2)^2}} \quad (2)$$

$$L3 = \frac{\sqrt{(x2-x1)^2 + (Y2-y1)^2}}{\sqrt{(x1-x2)^2 + (y1-y2)^2}} \quad (3)$$

$$L4 = \frac{\sqrt{(X2-x8)^2 + (Y2-y8)^2}}{\sqrt{(x1-x2)^2 + (y1-y2)^2}} \quad (4)$$

Each of the feature distances L1, L2, L3 and L4 is found by dividing the prescriptive distance by the distance between the inner corners of both eyes based on an anatomical knowledge that the positions of inner corners of both eyes do not vary with muscular contraction even though the driver changes his or her expression or becomes drowsy. Each prescriptive distance is expressed as a relative value with reference to the distance between the inner corners of eyes using this distance as a divisor. Accordingly, the process accurately recognizes a change in the prescriptive distance even when the face position changes in the overall length direction of the vehicle.

It should be noted that in Equation (2), X1 and Y1 denote X1=(b−d)/(c−a) and Y1=aX1+b or cX1+d. Also in Equation (2), a=(y3−y1)/(x3−x1), b=y1−a*x1 or y3−a*x3, c=−1/a, and d=y6−c*x6. In Equations (3) and (4), X2 and Y2 denote X2=(b−d)/(c−a) and Y2=aX2+b or cX2+d. Also in Equations (3) and (4), a=(y1−y2)/(x1−x2), b=y1−a*x1 or y2−a*x2, c=−1/a, and d=y8−c*x8.

Within the scientific knowledge of anatomy it is generally considered that the muscular contraction does not change the positions of the inner and outer corners of eyes even when the driver changes his or her expression or becomes drowsy. Thus the exemplary process converts coordinates of the feature point into the coordinate system mainly including the reference line connecting the inner and outer corners of eyes and the axis perpendicular to the reference line. The system then calculates the second feature distance L2, the third feature distance L3, and the fourth feature distance L4. The purpose is to accurately recognize a change in the distance even when the face tilts, for example. The system stores the calculated feature distances in the RAM 10b based on categories.

At S1340, the process increments the first counter by one and proceeds to S1350. The process determines whether the first counter value is greater than or equal to a first predetermined prescriptive count. In the present embodiment, the first prescriptive count corresponds to m in FIG. 7 and signifies the number of captured images that are acquired in five seconds and that are to be processed. When the first counter value is less than or equal to the first prescriptive count based on the determination, the process returns to S1320. When the first counter value exceeds the first prescriptive count, the process proceeds to S1360.

At S1360, the process extracts a number of the feature distances L1, L2, L3 and L4 stored in the RAM 10b equal to the first prescriptive count in a chronological order starting from the one most recently stored in the RAM 10b. The process uses the extracted feature distance to find a frequency distribution on left and right parts of the face. The process calculates an average value in accordance with the frequency distribution. The process categorizes the average values into representative feature distances L1a, L2a, L3a and L4a and stores them in the RAM 10b.

At S1370, the process increments the second counter by one and proceeds to S1380. The process determines whether the second counter value is greater than or equal to a first predetermined setup count. In the present embodiment, the first setup count corresponds to n in FIG. 7 and signifies the number of representative feature distances calculated in 30 seconds. When the second counter value is less than or equal to the first setup count based on the determination, the process returns to S1320. When the second counter value exceeds the first setup count, the process deletes the feature point positions and the feature distances L1, L2, L3 and L4 stored in the RAM 10b and returns to the wakeful face feature collection process.

The feature distance calculation process uses the captured image to acquire a feature point and calculate a feature distance. An emotion expression determination process, to be described in greater detail hereinafter, uses the calculated feature distance to calculate n representative feature distances L1a, L2a, L3a and L4a used as a criterion for determining whether the face of the driver expresses the emotion.

Figure 8:
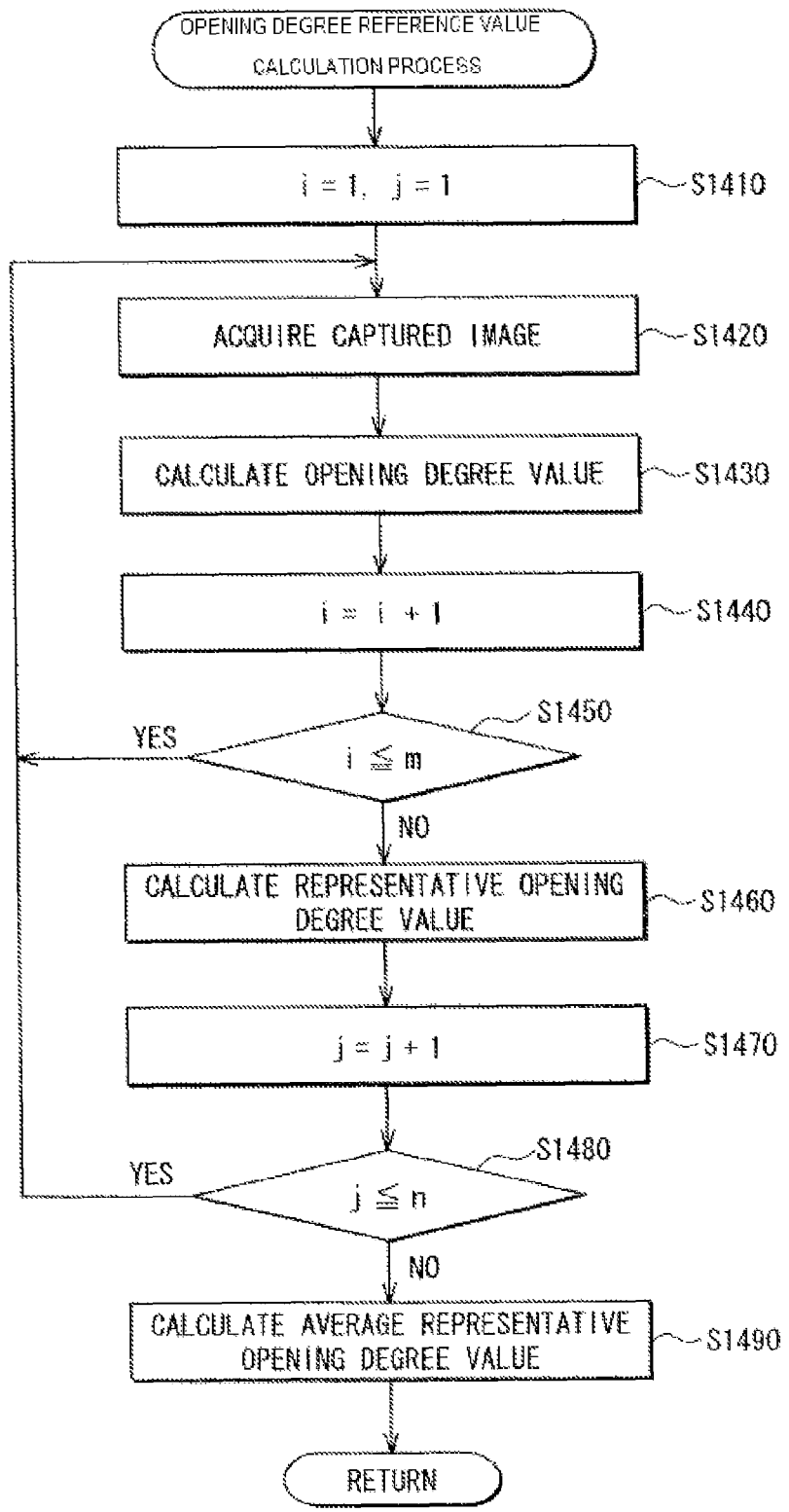
FIG. 8 is a flowchart illustrating portions of an exemplary opening degree reference value calculation process.

The opening degree reference value calculation process shown in the flowchart of FIG. 8 and described herein starts at S1410. At S1410, a first counter "i" and a second counter "j" are each set to an initial value, such as one, in accordance with the present embodiment. At S1420, the process acquires a captured image from the camera 20. At S1430, the captured image processed and multiple predetermined feature points from left and right parts of the face are extracted. Based on the extracted feature points, the process calculates opening degree values L for the left and right parts of the face and stores them in the RAM 10b.

According to the embodiment, as shown in FIG. 3, the process extracts the following feature points: an upper eyelid top (x6, y6), a lower eyelid bottom (x7, y7), i.e., a boundary between an eyelid and part of an eyeball farthest from the parietal region, and inner corners of both eyes (x1, y1) and (x2, y2). Using equation (5), the process calculates an opening degree value L when the driver is in the resting open eye state.

$$L = \frac{\sqrt{(x6 - x7)^2 + (y6 - y7)^2}}{\sqrt{(x1 - x2)^2 + (y1 - y2)^2}} \quad (5)$$

According to the embodiment, the opening degree value L is found by dividing a distance between the upper eyelid top and the lower eyelid bottom by a distance between the inner corners of both eyes.

At S1440, the process increments the first counter by one and proceeds to S1450. The process determines whether the first counter value is smaller than a second predetermined prescriptive count. In the embodiment, the second prescriptive count corresponds to m in FIG. 8 and signifies the number of captured images that are acquired in five seconds and are to be processed. When the first counter value is less than or equal to the second prescriptive count based on the determination, the process returns to S1420. When the first counter value exceeds the second prescriptive count, the process proceeds to S1460.

At S1460, the process extracts a number of the opening degree values L stored in the RAM 10b equal to the second prescriptive count in a chronological order starting from the one most recently stored in the RAM 10b. Using the extracted opening degree values L, the process finds frequency distributions for the left and right parts of the face. Based on the frequency distributions, the process extracts a class value whose cumulative relative frequency is around 5% higher than the minimum value. The process stores the extracted class value as a representative opening degree value La in the RAM 10b. It should be noted that each class is pre-assigned with an optimal value for the second prescriptive count.

According to the embodiment, the system uses an analysis of the frequency distribution to extract a value of an eye opening degree associated with class value whose cumulative relative frequency is about 5% higher than the minimum value. In other words, a value of eye opening degree at or near the 5$^{th}$ percentile of cumulative relative frequency based on the total sample of eye opening degrees is extracted. The system assumes the extracted value to be the representative opening degree value La. The representative opening degree La is assumed to be the smallest of opening degree values L and is considered to be representative of drowsiness. By selecting a 5$^{th}$ percentile value, outlying values that are calculated from an image captured, for example, when the driver blinks or closes their eyes purposefully are excluded since such situations are not normally considered to be associated with drowsiness, particularly if they are transient in nature.

At S1470, the process increments the second counter by one and proceeds to S1480. The process determines whether the second counter value is greater than or equal to a second predetermined setup count. In the present embodiment, the second setup count corresponds to n in FIG. 8 and signifies the number of representative opening degree values calculated in 30 seconds. When the second counter value is less than or equal to the second setup count based on the determination, the process returns to S1420. When the second counter value exceeds the second setup count, the process proceeds to S1490.

At S1490, the process averages the representative opening degree values La stored in the RAM 10b to calculate an average representative opening degree value Laa and store it in the RAM 10b. The process then deletes the opening degree value L and the representative opening degree value La stored in the RAM 10b, initializes the first and second counter values, and returns to the wakeful face feature collection process.

The wakefulness reference value calculation process uses a captured image to calculate the opening degree value L. The process uses opening degree values L as many as the second prescriptive count to find a frequency distribution. As described above, the process analyzes the frequency distribution to extract a class value having a cumulative relative frequency around 5% higher than the minimum value. The system assumes the extracted class to be the representative opening degree value La. Based on the representative opening degree values La as many as the second setup count, the process calculates an average representative opening degree value Laa, an index for the wakefulness degree criterion calculation process to calculate a wakefulness degree criterion.

Figure 9:
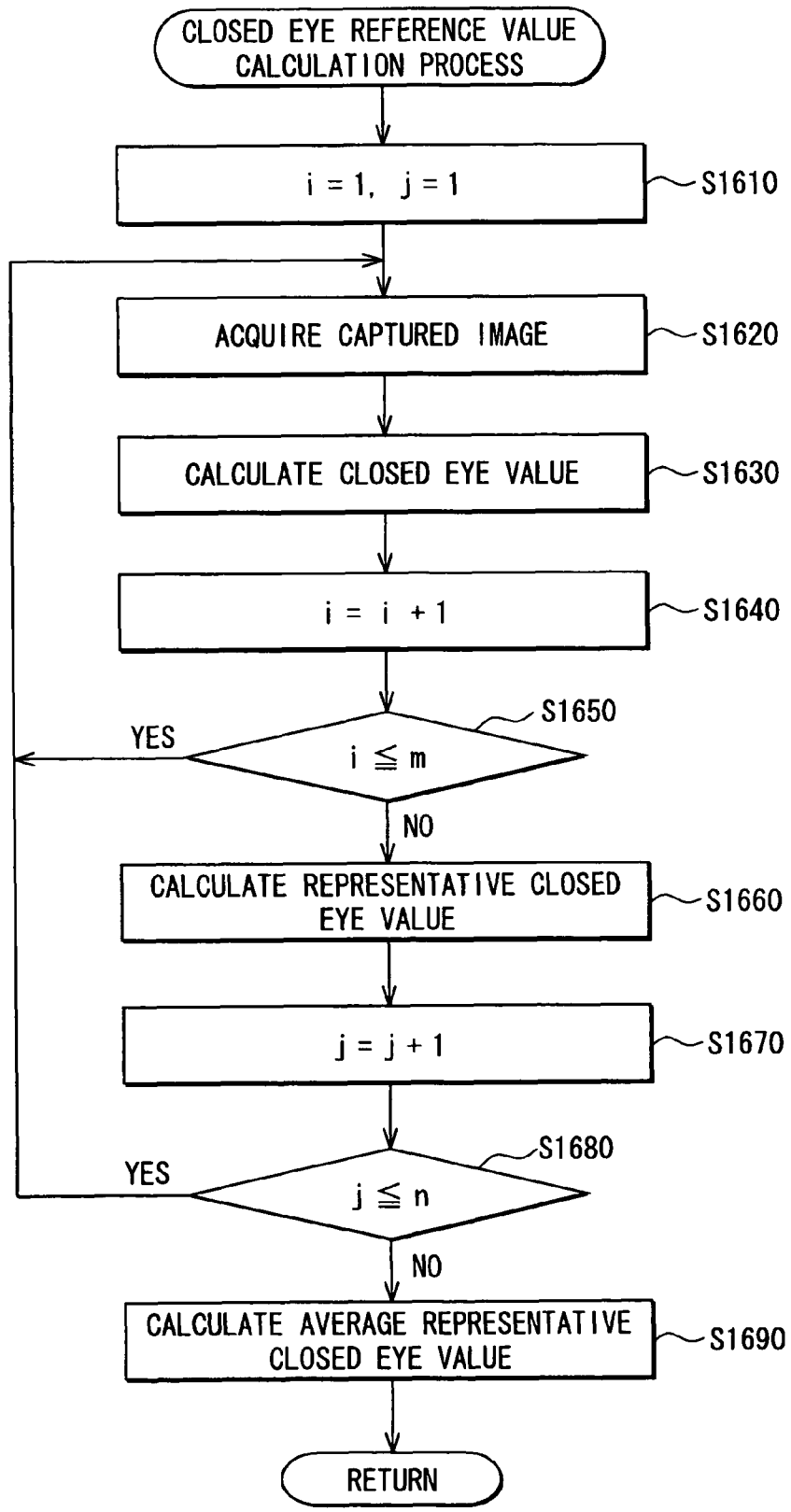
FIG. 9 is a flowchart illustrating portions of an exemplary open eye reference value calculation process.

A closed eye reference value calculation process of the wakeful face feature collection process is shown and described in connection with the flowchart of FIG. 9 and starts at S160. At S1610, the process sets a first counter "i" and a second counter "j" to initial values such as 1 s according to the present embodiment. At S1620, the process acquires or otherwise captures an image from the camera 20. At S1630, the captured image is processed and the inner corners of both eyes at (x1, y1) and at (x2, y2), the upper eyelid top at (x6, y6), and the lower eyelid bottom at (x7, y7) are extracted from left and right parts of the facial image. Using equation (5), the opening degree values L, such as closed eye values, on the left and right parts of the face are calculated and stores the values in the RAM 10b.

At S1640, the process increments the first counter by one and proceeds to S1650. When the first counter value is less than or equal to the second predetermined prescriptive count m in FIG. 9, the process returns to S1620. When the first counter value exceeds the second prescriptive count, the process proceeds to S1660.

At S1660, the process extracts the closed eye values L stored in the RAM 10b as many as the second prescriptive count in a chronological order starting from the one that is most recently stored in the RAM 10b. Using the extracted opening degree values L, the process finds frequency distributions for the left and right parts of the face. The process calculates an average value of the closed eye values L in accordance with the frequency distribution and stores the value as a representative closed eye value Lc in the RAM 10b.

At S1670, the process increments the second counter by one and proceeds to S1680. When the second counter value is less than or equal to a second predetermined setup count n in FIG. 9, the process returns to S1620. When the second counter value exceeds the second setup count, the process proceeds to S1690.

At S1690, the process averages the representative closed eye values Lc stored in the RAM 10*b* to calculate an average representative closed eye value Lca and store it in the RAM 10*b*. The process then deletes the closed eye degree value L and the representative closed eye value Lc stored in the RAM 10*b*, initializes the first and second counter values, and returns to the wakeful face feature collection process.

The closed eye reference value calculation process uses a captured image to calculate the closed eye value L. The process calculates an average value of the closed eye values L as many as the second prescriptive count and assumes the average value to be the representative closed eye value Lc. Based on the representative closed eye values Lc as many as the second setup count, the process calculates an average representative closed eye value Lca, an index for the wakefulness degree criterion calculation process to calculate a wakefulness degree criterion.

Figure 10:
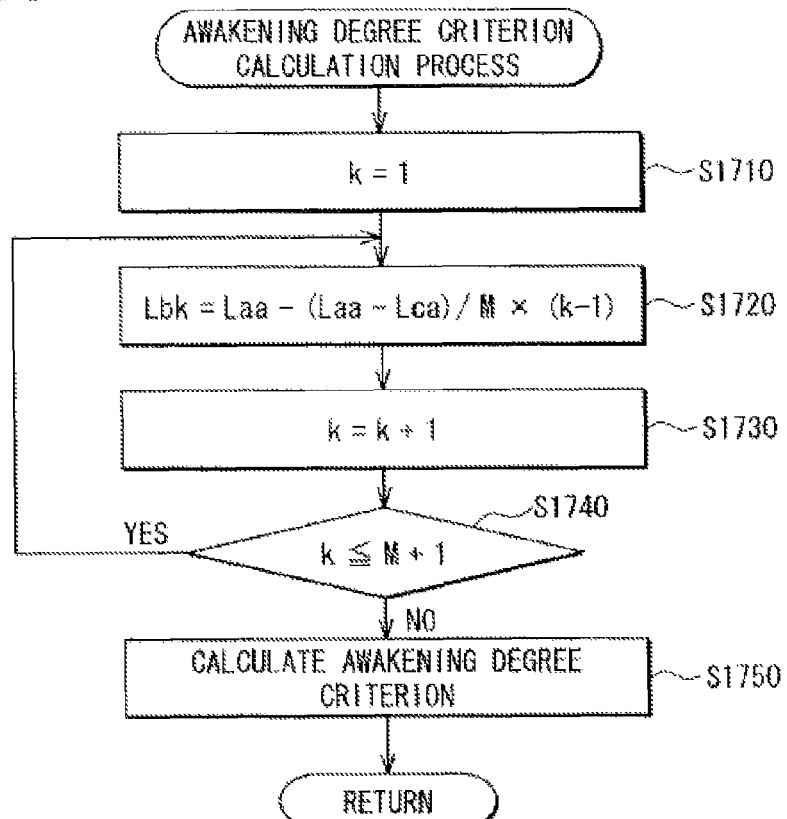
FIG. 10 is a flowchart illustrating portions of an exemplary wakefulness determination reference value calculation process.

A wakefulness degree criterion calculation process of the wakeful face feature collection process shown and described in connection with the flowchart in FIG. 10 starts at S170. At S1710, the process sets a detection counter k to an initial value such as 1 according to the present embodiment. At S1720, the process acquires the average representative opening degree value Laa and the average representative closed eye value Lca stored in the RAM 10*b* by the wakefulness reference value calculation process and the closed eye reference value calculation process. Using Equation (6), the process calculates criterion values Lbk of left and right parts of the face and stores the criterion values Lbk in the RAM 10*b*.

$$Lbk = Laa - (Laa - Lca)/M \times (k-1) \quad (6)$$

where M is the number of drowsiness levels minus one determined by a drowsiness level determination process, to be described in greater detail hereinafter, and k is a count value in the detection counter.

At S1730, the process increments the detection counter k by one and proceeds to S1740. The process determines whether the detection counter value is smaller than a predetermined prescriptive count value such as 4 in the present embodiment, such as the number of drowsiness levels M incremented by one. When the detection counter value is less than or equal to the prescriptive count value, the process returns to S1720. When the detection counter value exceeds the prescriptive count value, the process proceeds to S1750.

At S1750, the process calculates first through third wakefulness degree criteria Lk1, Lk2, Lk3 for left and right parts of the face based on the criterion values Lb1 Lb2, Lb3, and Lb4) stored in the RAM 10*b*. The process stores the first through third wakefulness degree criteria Lk1, Lk2, Lk3 in the RAM 10*b*.

The first wakefulness degree criterion Lk1 is an average of the criterion value Lb1 and the criterion value Lb2. The second wakefulness degree criterion Lk2 is an average of the criterion value Lb2 and the criterion value Lb3. The third wakefulness degree criterion Lk3 is an average of the criterion value Lb3 and the criterion value Lb4. The process then returns to the wakeful face feature collection process.

The wakefulness reference value calculation process calculates the average representative opening degree value Laa. The open eye reference value calculation process calculates the average representative open eye value Lca. Based on the values Laa and Lca, the wakefulness degree criterion calculation process calculates the wakefulness degree criteria Lk1, Lk2 and Lk3 used for a drowsiness level determination process, to be described in greater detail hereinafter, to estimate the wakefulness degree of the driver.

Figure 11:
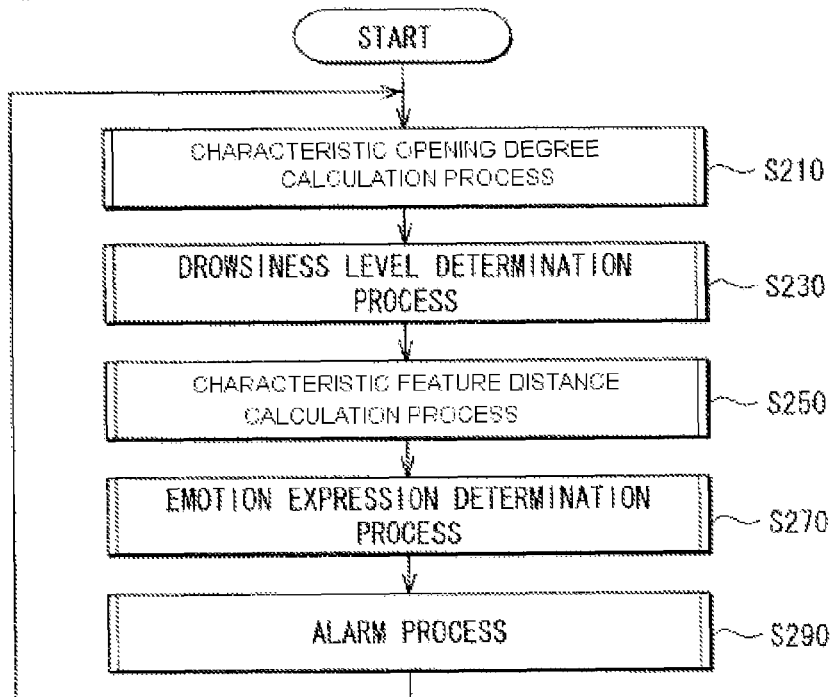
FIG. 11 is a flowchart illustrating portions of an exemplary doze alarm process.

A doze alarm process as shown and described in connection with FIG. 11 can be performed by the CPU 10*c* of the wakefulness degree calculation apparatus and starts when the system-mounted vehicle starts, such as when an engine starts according to the present embodiment. At S210, a characteristic opening degree calculation process is performed that calculates an opening degree value for the driver during driving and, based on the opening degree value, calculates a characteristic opening degree value of the driving feature values used for estimating the wakefulness degree of the driver.

At S230, a drowsiness level determination process is performed that estimates the wakefulness degree of the driver and determines the drowsiness level based on the characteristic opening degree value calculated at S210 and the wakefulness degree criterion calculated by the wakefulness degree criterion calculation process. At S250, a characteristic feature distance calculation process is performed that calculates a feature distance of the driver during driving and, according to the feature distance, calculates a characteristic feature distance of the driving feature values used for determining whether the driver expresses an emotion. At S270, an emotion expression determination process is performed that determines whether the driver expresses the emotion based on the characteristic feature distance calculated by the characteristic feature distance calculation process and the average representative feature distance calculated by the feature distance calculation process.

At S290, an alarm process is performed that determines a level of alarm to be generated and generates the determined alarm based on the drowsiness level determined by the drowsiness level determination process and a determination result of the emotion expression determination process. The process then returns to S210 and repeats Steps S210 through S290 until the system-mounted vehicle stops operating.

Figure 12:
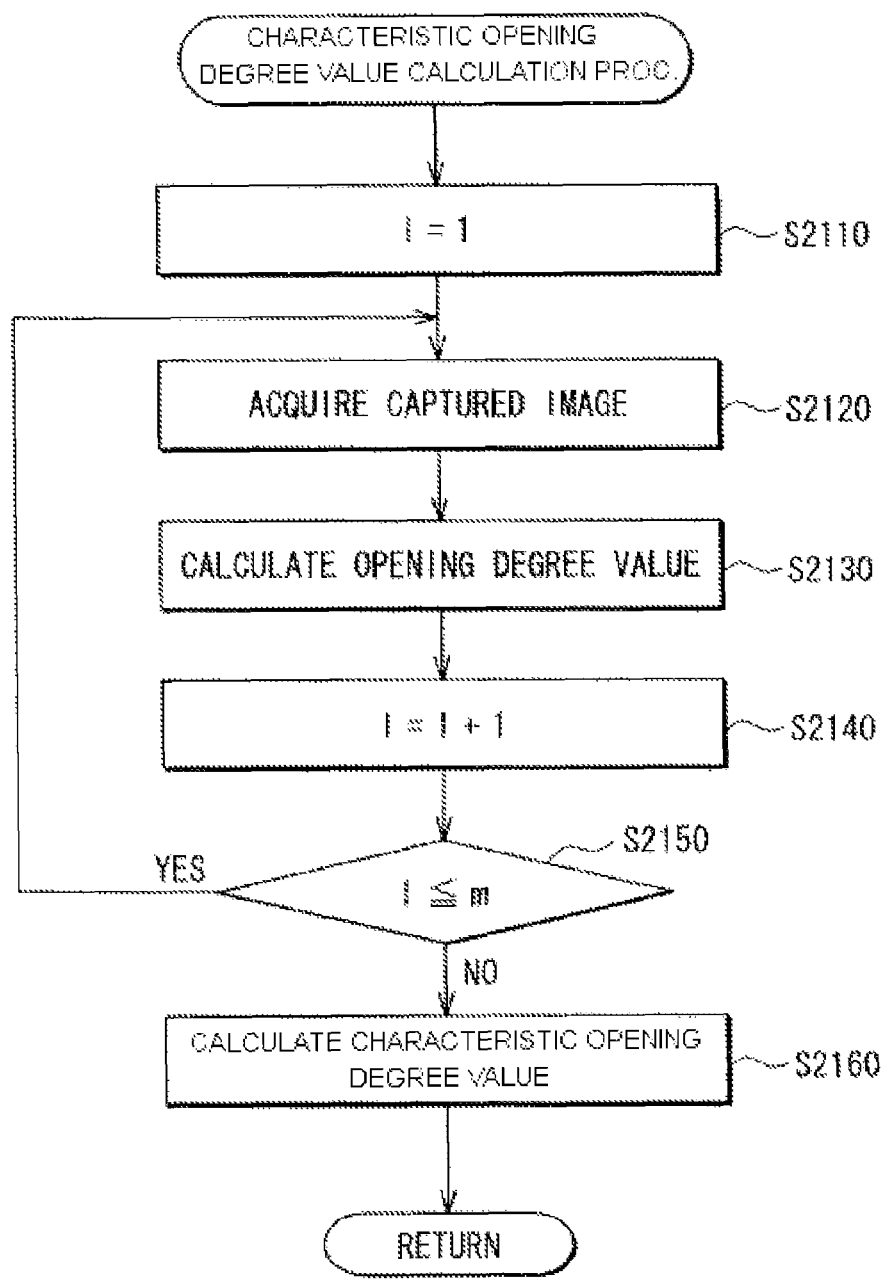
FIG. 12 is a flowchart illustrating portions of an exemplary characteristic opening degree value calculation process.

A characteristic opening degree value calculation process shown and described in connection with the flowchart of FIG. 12 is performed at S210 of the doze alarm process. At S2110 after initiation, the characteristic opening degree value calculation process sets a first counter "i" to an initial value such as 1 according to the present embodiment. At S2120, the process captures or otherwise acquires an image from the camera 20. At S2130, the captured image is processed and the inner corners of both eyes (x1, y1) and (x2, y2), the upper eyelid top (x6, y6), and the lower eyelid bottom (x7, y7) are extracted from left and right parts of the face. Using equation (5), the opening degree values L on the left and right parts of the face and stores the values in the RAM 10*b* are calculated.

At S2140, the first counter is incremented by one and execution proceeds to S2150. It is determined whether the first counter value is less than or equal to a predetermined second prescriptive count m in FIG. 12. When the first counter value is less than or equal to the second prescriptive count based on the determination, the process returns to S2120. When the first counter value exceeds the second prescriptive count, the process proceeds to S2160.

At S2160, the process extracts the opening degree values L stored in the RAM 10*b* as many as the second prescriptive count in a chronological order starting from the one that is most recently stored in the RAM 10*b*. Using the extracted opening degree values L, the process finds frequency distributions for the left and right parts of the face. As described above, based on analyzing the frequency distributions, a class value in the 5$^{th}$ percentile is extracted. The process stores the extracted class value as a characteristic opening degree value Ld in the RAM 10*b*. It should be noted that each class is preassigned with an optimal value for the second prescriptive count. The process then returns to the doze alarm process.

Figure 13:
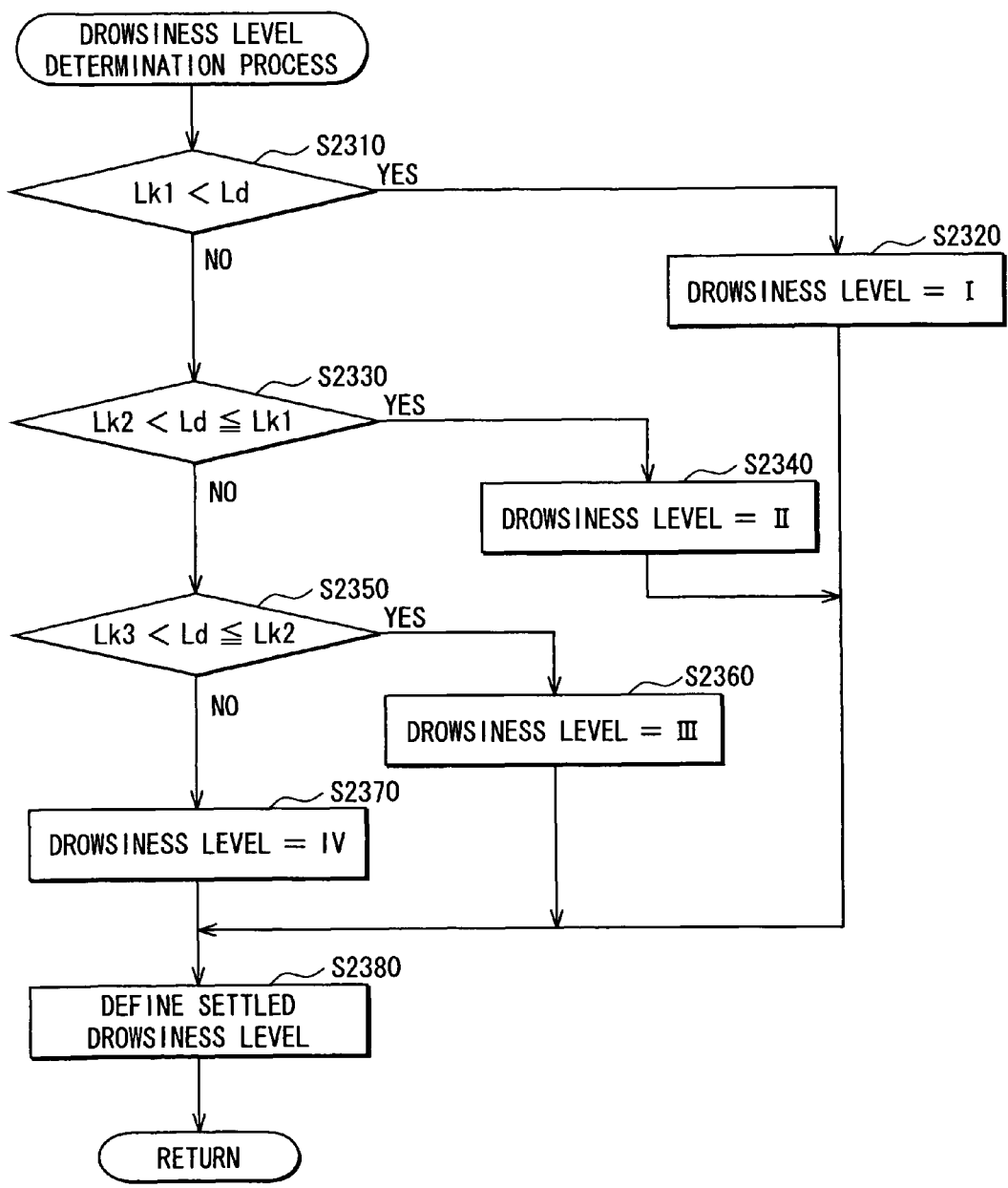
FIG. 13 is a flowchart illustrating a drowsiness level determination process.

A drowsiness level determination process as shown in described in connection with the flowchart of FIG. 13, is performed at S230 of the doze alarm process. At S2310 after initiation, the drowsiness level determination process determines whether the characteristic opening degree value Ld calculated by the characteristic opening degree value calculation process is greater than the first wakefulness degree criterion Lk1 stored in the RAM 10*b*.

When the characteristic opening degree value Ld is greater than the first wakefulness degree criterion Lk1 based on the determination, the process proceeds to S2320. The process assumes that the driver does not feel drowsy and the wakefulness degree is high. The process sets the drowsiness level to 1 indicating a wakefulness state and proceeds to S2380. The drowsiness level indicates the wakefulness degree of the driver.

When the characteristic opening degree value Ld is less than or equal to the first wakefulness degree criterion Lk1 based on the determination at S2310, the process proceeds to S2330. The process determines whether the characteristic opening degree value Ld is greater than the second wakefulness degree criterion Lk2 stored in the RAM 10*b*. When characteristic opening degree value Ld is greater than the second wakefulness degree criterion Lk2 based on the determination, the process proceeds to S2340. The process assumes that the driver slightly feels drowsy. The process sets the drowsiness level to 2 indicating a slightly drowsy state and proceeds to S2380. To be slightly drowsy signifies a lower wakefulness degree than the wakefulness state.

When the characteristic opening degree value Ld is less than or equal to the second wakefulness degree criterion Lk2 based on the determination at S2330, the process proceeds to S2350. The process determines whether the characteristic opening degree value Ld is greater than the third wakefulness degree criterion Lk3 stored in the RAM 10*b*.

When the characteristic opening degree value Ld is greater than the third wakefulness degree criterion Lk3 based on the determination, the process proceeds to S2360. The process assumes that the driver intermediately feels drowsy. The process sets the drowsiness level to 3 indicating an intermediately drowsy state and proceeds to S2380. To be intermediately drowsy signifies a lower wakefulness degree than the slightly drowsy state.

When the characteristic opening degree value Ld is less than or equal to the third wakefulness degree criterion Lk3 based on the determination at S2350, the process proceeds to S2370. The process assumes that the driver seriously feels drowsy. The process sets the drowsiness level to 4 indicating a seriously drowsy state and proceeds to S2380. To be seriously drowsy signifies a lower wakefulness degree than the intermediately drowsy state.

The process from Steps S2310 to S2370 uses the characteristic opening degree values Ld for the left and right parts of the face and the corresponding wakefulness degree criteria. That is, the drowsiness level is settled for each of both eyes. At S2380, a settled drowsiness level is defined. Settled drowsiness is a drowsiness level indicative of a low wakefulness degree out of the drowsiness levels determined correspondingly to the characteristic opening degree values Ld for the left and right parts of the face. The process then returns to the doze alarm process.

The characteristic opening degree value calculation process calculates characteristic opening degree values Ld for the left and right parts of the face. The drowsiness level determination process estimates a drowsiness level by comparing the characteristic opening degree values Ld with the first through third wakefulness degree criteria Lk1, Lk2 and Lk3. The process defines a settled drowsiness level equivalent to a drowsiness level indicative of a low wakefulness degree out of the drowsiness levels estimated correspondingly to the characteristic opening degree values Ld for the left and right parts of the face.

Figure 14:
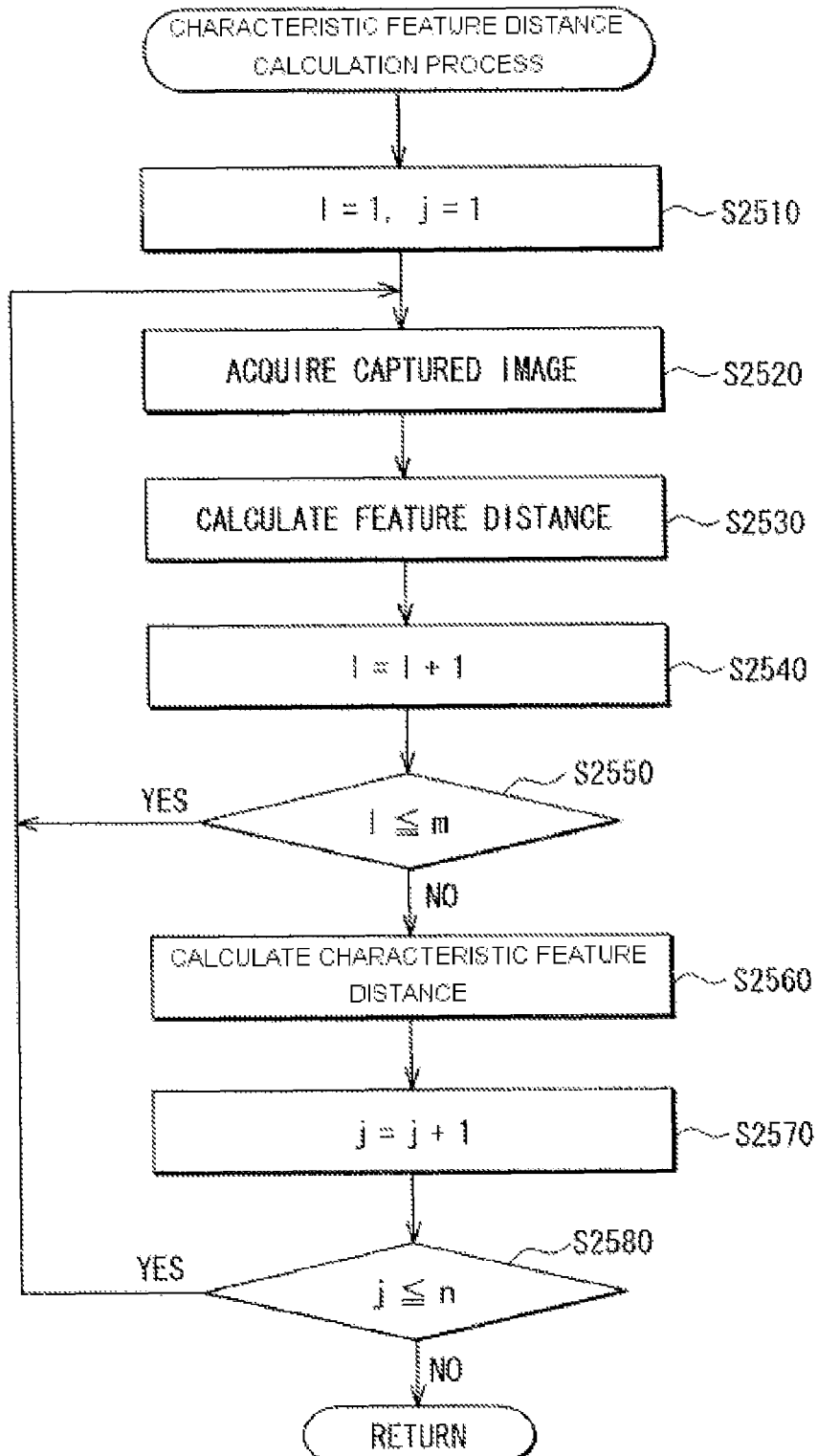
FIG. 14 is a flowchart illustrating a characteristic feature distance calculation process.

The characteristic feature distance calculation process, shown and described in connection with the flowchart of FIG. 14, is performed at S250 of the doze alarm process. At S2510 after initiation, the characteristic feature distance calculation process sets a first counter "l" and a second counter "j" to initial values such as 1 s according to the present embodiment.

At S2520, the process acquires or otherwise captures an image from the camera 20. At S2530, the captured image is processed, the first through fourth feature distances, L1, L2, L3 and L4, for the left and right parts of the face are calculated, and the calculated feature distances are stored in the RAM 10*b* based on categories. At S2540, the first counter is incremented by one and execution proceeds to S2550. When the first counter value is less than or equal to a predetermined first prescriptive count m in FIG. 14, the process returns to S2520. When the first counter value exceeds the first prescriptive count, the process proceeds to S2560. At S2560, a number of the feature distances stored in the RAM 10*b* are extracted in an amount equaling the first prescriptive count in a chronological order starting from the one most recently stored in the RAM 10*b*. The process uses the extracted feature distances to find frequency distributions for the left and right parts of the face. The process extracts mode values in accordance with the frequency distributions. The process stores the mode values as the characteristic feature distances L1*d*, L2*d*, L3*d* and L4*d* in the RAM 10*b*.

At S2570, the process increments the second counter by one and proceeds to S2580. When the second counter value is less than or equal to a predetermined first setup count n in FIG. 14, the process returns to S2520. When the second counter value exceeds the first setup count, the process deletes the feature distances L1, L2, L3, and L4 stored in the RAM 10*b* and returns to the doze alarm process.

Similarly to the feature distance calculation process, the characteristic feature distance calculation process acquires deposition positions based on a captured image and calculates a feature distance. Based on the calculated feature distance, the process calculates n characteristic feature distances L1*d*, L2*d*, L3*d*, and L4*d* as indexes for the emotion expression determination process to determine whether the face of the driver expresses the emotion.

Figure 15:
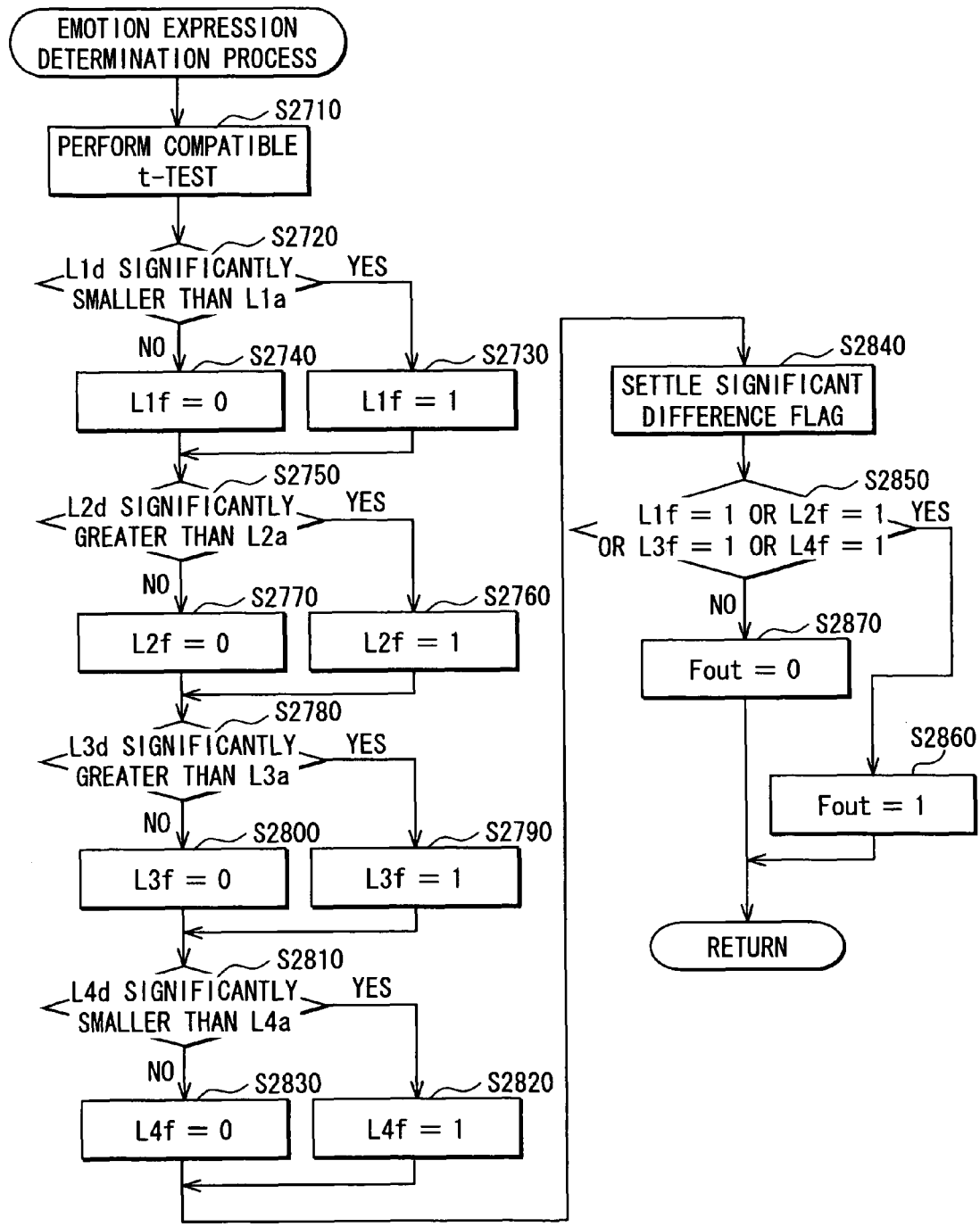
FIG. 15 is a flowchart illustrating an emotion expression determination process.

An emotion expression determination process shown and described in connection with the flowchart of FIG. 15 is performed at S270 of the doze alarm process. The RAM 10 stores the characteristic feature distances L1*d*, L2*d*, L3*d* and L4*d* and the representative feature distances L1*a*, L2*a*, L3*a* and L4*a* as many as the first setup count found for the left and right parts of the face. At S2710 after initiation, the emotion expression determination process performs compatible t-tests for the corresponding feature distances assuming that a significant level for the compatible t-test is 5%.

In other words, at S2710, the process determines whether each of the left and right parts of the face shows a change in the feature distance during driving from the feature distance in an awaked state, such as before driving, over a predetermined range.

At S2720, the process determines whether the first characteristic feature distance L1$d$ is significantly shorter than the representative feature distance L1$a$ based on the compatible t-test at S2710. When the first characteristic feature distance L1$d$ is significantly short, such as when the first feature distance L1 is shorter than the awaked state, the process proceeds to S2730. When the first characteristic feature distance L1$d$ is not significantly short based on the determination, the process proceeds to S2740.

At S2730, the process sets a first flag L1$f$ to a high, set, or true value, such as L1$f$=1. At S2740, the process sets the first flag L1$f$ to a low, reset or false value L1$f$=0. The process then proceeds to S2750. The first flag L1$f$ indicates whether the first feature distance L1 becomes short. The first flag L1$f$ set to high shows that the first feature distance L1 becomes short based on, for example, the corrugator muscle contracting. The first flag L1$f$ is set to low and shows that the first feature distance L1 is unchanged, resulting from a lack of contraction of the corrugator muscle does not contract.

At S2750, the process determines whether the second characteristic feature distance L2$d$ is significantly larger than the second representative feature distance L2$a$ based on the compatible t-test at S2710. When the second characteristic feature distance L2$d$ is significantly large, such as when the upper eyelid is raised more than the awaked state, the process proceeds to S2760. When the second characteristic feature distance L2$d$ is not significantly large based on the determination, the process proceeds to S2770.

At S2760, the process sets a second flag L2$f$ to a high, set, or true value, such as L2$f$=1. At S2770, the process sets the second flag L2$f$ to a low, reset, or false value, such as L2$f$=0. The process then proceeds to S2780. The second flag L2$f$ indicates whether or not the second feature distance L2 becomes short. The second flag L2$f$ set to high shows that the second feature distance L2 becomes long, based on for example, the levator palpebrae superioris contracts. The second flag L2$f$ set to low shows that the second feature distance L2 is unchanged, such as the condition where the levator palpebrae superioris does not contract.

At S2780, the process determines whether the third characteristic feature distance L3$d$ is significantly larger than the third representative feature distance L3$a$ based on the compatible t-test at S2710. When the third characteristic feature distance L3$d$ is significantly large, such as when the third feature distance L3 becomes longer than the awaked state, the process proceeds to S2790. When the third characteristic feature distance L3$d$ is not significantly large based on the determination, the process proceeds to S2800.

At S2790, the process sets a third flag L3$f$ to a high, set, or true value, such as L3$f$=1. At S2800, the process sets the third flag L3$f$ to a low, reset, or false value, such as L3$f$=0. The process then proceeds to S2810. The third flag L3$f$ indicates whether or not the third feature distance L3 becomes long. The third flag L3$f$ set to high shows that the third feature distance L3 becomes long, such as the condition where the greater zygomatic muscle or the risorius muscle contracts. The third flag L3$f$ set to low shows that the third feature distance L3 is unchanged, such as the condition where the greater zygomatic muscle and the risorius muscle do not contract.

At S2810, the process determines whether the fourth characteristic feature distance L4$d$ is significantly shorter than the fourth representative feature distance L4$a$ based on the compatible t-test at S2710. When the fourth characteristic feature distance L4$d$ is significantly short, such as when the fourth representative feature distance L4$a$ is shorter than the awakened state, the process proceeds to S2820. When the fourth characteristic feature distance L4$d$ is not significantly short based on the determination, the process proceeds to S2830.

At S2820, the process sets a fourth flag L4$f$ to a high, set or true value such as L4$f$=1. At S2830, the process sets the fourth flag L4$f$ to a low, reset or false value such as L4$f$=0. The process then proceeds to S2840. The fourth flag L4$f$ indicates whether the fourth feature distance L4 becomes short. The fourth flag L4$f$ set to high shows that the fourth feature distance L4 becomes short, such as the condition where the greater zygomatic muscle or the risorius muscle contracts. The fourth flag L4$f$ set to low shows that the fourth feature distance L4 is unchanged, such as the condition where the greater zygomatic muscle and the risorius muscle do not contract.

The first through fourth flags set at S2710 through S2830 may be differently set for the feature distances L1, L2, L3, and L4 on the left and right parts of the face. When the feature distance is set to a large value, the process sets the flag at S2840 assuming that the corresponding muscle contracts. The set flag is hereafter also referred to as a significant difference flag indicating a significant difference between a feature distance on the left side as compared to a features distance on the right side. Accordingly, when a flag associated with the right or left sides is set to "1" corresponding to a respective contraction of the corresponding muscle, the process sets a significant difference flag to "1" at S2840.

At S2850, the process determines whether any of the significant difference flags set at S2840 indicates a change of the feature distances L1, L2, L3, and L4 in comparison with the awaked state. When any one of the feature distances L1, L2, L3, and L4 changes it can be determined that any one of the corrugator muscle, the levator palpebrae superioris, the greater zygomatic muscle, and the risorius muscle contracts, whereupon the process proceeds to S2860.

At S2860, the process sets an emotion flag Fout that is used for the alarm process to a high, set or true value such as Fout=1, and returns to the doze alarm process. When none of the corrugator muscle, the levator palpebrae superioris, the greater zygomatic muscle, and the risorius muscle contracts based on the determination at S2850, the process proceeds to S2870. At S2870, the process sets the emotion flag Fout to a low, reset or false value Fout=0 and returns to the doze alarm process.

The emotion flag Fout indicates whether the face expresses a specific emotion. According to the specific emotion, a change in the opening degree value L indicates a tendency similar to a decrease in the wakefulness degree. The emotion flag Fout set to high indicates that the face expresses the specific emotion. The emotion flag Fout set to low indicates that the face does not express the specific emotion.

That is, the emotion expression determination process estimates contraction of the corrugator muscle according to a variation in the first feature distances L1 before and during driving. The process estimates contraction of the levator palpebrae superioris according to a variation in the second feature distances L2 before and during driving. The process estimates contraction of the greater zygomatic muscle or the risorius muscle according to a variation in the third feature distances L3 before and during driving. The process estimates contraction of the greater zygomatic muscle or the risorius muscle according to a variation in the fourth feature distances L4 before and during driving. The process determines that the face expresses the specific emotion when any one of the corrugator muscle, the levator palpebrae superioris, the greater zygomatic muscle, and the risorius muscle contracts.

Figure 16:
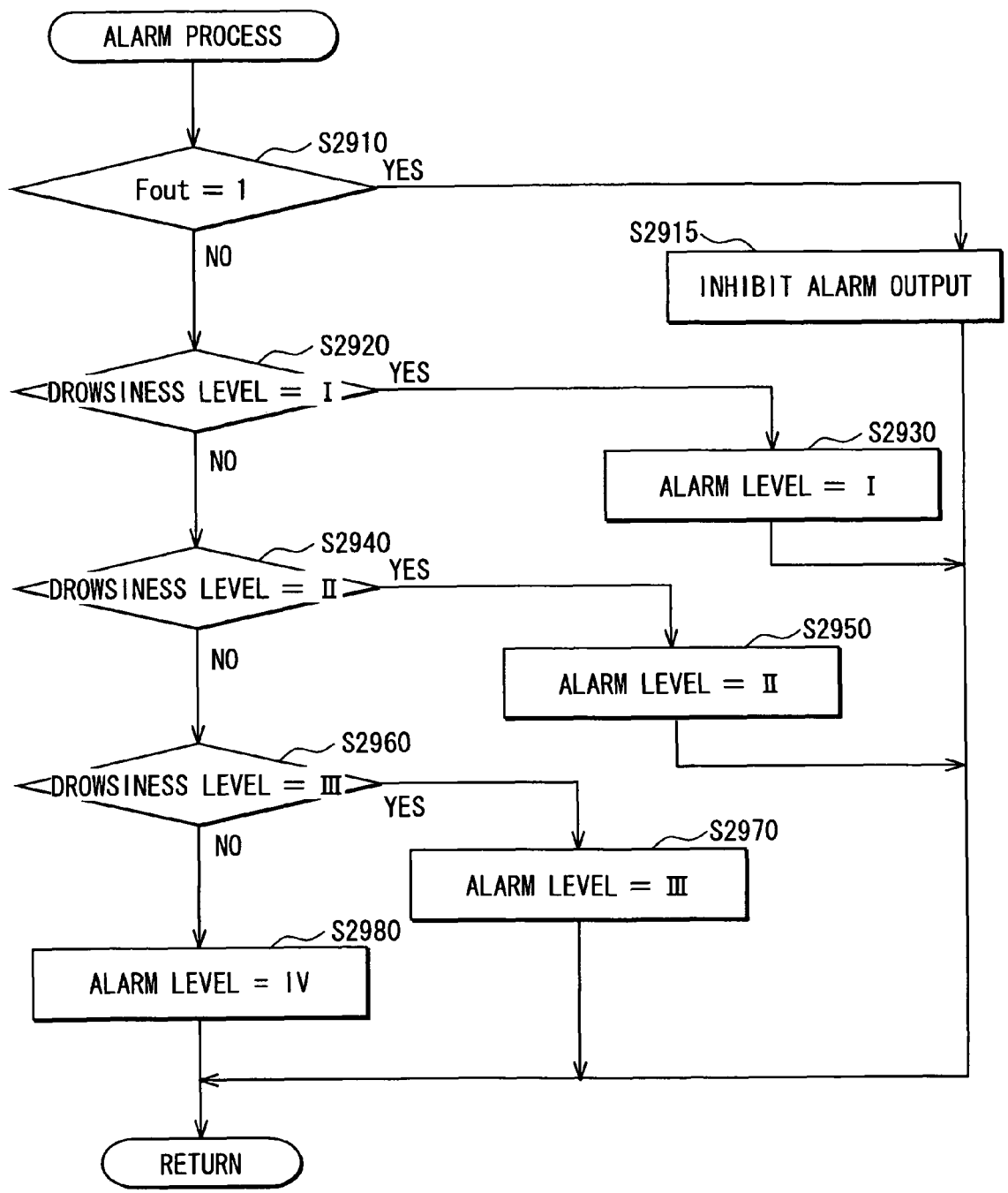
FIG. 16 is a flowchart illustrating an alarm process.

The alarm process shown and described in connection with the flowchart of FIG. 16 is a performed at S290 of the doze alarm process. At S2910 after initiation, the alarm process determines whether the face expresses the specific emotion according to the emotion flag set in the emotion expression determination process. When the face expresses the specific emotion based on the determination, the process proceeds to S2915. The alarm output is inhibited such that no audio or video signal is transmitted to the speaker 16 or the monitor 17, and execution returns to the doze alarm process.

When the face does not express the specific emotion based on the determination, the process proceeds to S2920. At S2920, it is determined whether the drowsiness level determination process sets the settled drowsiness level to 1. When the settled drowsiness level is set to 1 based on the determination, the process proceeds to S2930.

At S2930, assuming the driver to be awake, the process allows the speaker 16 to output a driving advice such as "Drive carefully" and allows the monitor 17 to display an image showing that the driver is awake. The process then returns to the doze alarm process.

When the settled drowsiness level is set otherwise than 1 based on the determination at S2920, the process proceeds to S2940. At S2940, the process determines whether the settled drowsiness level is set to 2. When the settled drowsiness level is set to 2 based on the determination, the process proceeds to S2950.

At S2950, assuming the driver to be slightly drowsy, the process increases the wakefulness degree from the slightly drowsy state to the wakefulness state. The process allows the speaker 16 to output a stimulus sound and allows the monitor 17 to display an image showing that the driver is slightly drowsy. In addition, the process transmits a control instruction to the cool air supply apparatus 21 and allows it to apply cool air to the neck of the driver. The process then returns to the doze alarm process.

When the settled drowsiness level is set to a value other than 1 and 2 based on the determination at S2940, the process proceeds to S2960 a determination is made as to whether the settled drowsiness level is set to 3. When the settled drowsiness level is set to 3 based on the determination, the process proceeds to S2970.

At S2970, assuming the driver to be intermediately drowsy, the process allows the speaker 16 to output an alarm sound for advising the driver to refrain from driving and allows the monitor 17 to display an image showing that the driver is intermediately drowsy. In addition, the process transmits a control instruction to the seat belt wind-up apparatus 25 and allows it to wind up the seat belt tighter than usual. The process then returns to the doze alarm process.

When the settled drowsiness level is not set to 1, 2, or 3 based on the determination at S2960, the process assumes the level to be set to 4 and proceeds to S2980 where the driver is assumed to be seriously drowsy. The speaker 16 is allowed to output an alarm sound for advising the driver to stop driving and allows the monitor 17 to display an image showing that the driver is seriously drowsy. In addition, the process transmits a control instruction to the brake control apparatus 27 and then returns to the doze alarm process.

The alarm process returns to the doze alarm process without outputting an alarm when the emotion expression determination process determines that the face expresses the specific emotion. When it is determined that the face does not express the specific emotion, the wakefulness degree of the driver may decrease. In such case, the alarm process transmits signals to the speaker 16 and the monitor 17 for outputting alarms so as to increase the alarm level for the driver.

According to the present embodiment, S2120 of the characteristic opening degree value calculation process and S2520 of the characteristic feature distance calculation process are equivalent to an image acquisition means of the invention. The characteristic opening degree calculation process and the drowsiness level determination process are equivalent to a wakefulness estimate means of the invention. The alarm process is equivalent to an alarm means of the invention. The emotion expression determination process is equivalent to a specific emotion determination means of the invention. The affirmative determination at S2910 of the alarm process is equivalent to an inhibition means of the invention.

As mentioned above, the drowsiness alarm system 1 according to the present embodiment outputs no alarm when the emotion expression determination process determines that the face expresses a specific emotion. The drowsiness alarm system 1 can decrease the possibility of incorrectly issuing an alarm even when the specific emotion is simply expressed on the face. The drowsiness alarm system 1 can solve the problem that the wakefulness degree is incorrectly recognized to be lower than that actually felt by an occupant, that is a situation where drowsiness is recognized and an alarm condition generated even though the occupant feels no drowsiness. As a result, the drowsiness alarm system 1 can prevent a vehicle occupant from being worried about an alarm that is erroneously or incorrectly generated.

The feature distances L1, L2, L3, and L4 vary with contraction of one of the corrugator muscle, the levator palpebrae superioris, the greater zygomatic muscle, and the risorius muscle. The drowsiness alarm system 1 uses the feature distances to determine whether the specific emotion is expressed. The drowsiness alarm system 1 can determine many specific emotions such as uneasiness, anger, sadness, dazzle, surprise, and joy. The drowsiness alarm system 1 can more reliably decrease the possibility in which the wakefulness degree is incorrectly recognized to be low simply because the specific emotion is expressed.

Further, the drowsiness alarm system 1 uses the feature distances L1, L2, L3, and L4 to determine whether the face expresses the specific emotion. This determination is also referred to as an emotion expression. The drowsiness alarm system 1 can reduce process requirements compared to the conventional emotion expression process that compares a captured image with an image, reference image, feature template or the like for the expressed emotion.

When a large variation is found in the feature distances L1, L2, L3, and L4 for the left and right parts of the face, the drowsiness alarm system 1 uses the corresponding feature distance to determine whether the face expresses the specific emotion. The drowsiness alarm system 1 can improve the accuracy of determining whether the face expresses the specific emotion. When a person expresses his or her emotion only on the left or right part of the face, for example, the drowsiness alarm system 1 can determine whether the face expresses the specific emotion. When another person more remarkably expresses his or her emotion on the left or right part of the face than the other, the drowsiness alarm system 1 can reliably recognize that the face expresses the specific emotion.

The drowsiness alarm system 1 uses the opening degree value and the feature distance by dividing the distance between the upper eyelid top and the lower eyelid bottom and the prescriptive distance by the distance between the inner corners of eyes. The drowsiness alarm system 1 can accurately recognize variations in the opening degree value and the feature distance even when the face of the driver moves in the overall length direction of the vehicle.

Further, the drowsiness alarm system 1 converts feature point coordinates into the coordinate system with reference to the inner corner of eye and the outer corner of eye whose positions do not vary. Based on this coordinate system, the drowsiness alarm system 1 calculates the second feature distance L2, the third feature distance L3, and the fourth feature distance L4. The drowsiness alarm system 1 can accurately recognize variations in the feature distances even though the face of the driver tilts during driving.

While various exemplary embodiments are described herein, it is to be distinctly understood that the present invention is not limited thereto but may be otherwise variously embodied within the spirit and scope of the invention.

For example, the alarm process according to the above-mentioned embodiment inhibits the alarm output when the emotion flag indicates that the face expresses the specific emotion. The process may notify that the wakefulness degree is estimated inaccurately because the face expresses the specific emotion.

The doze alarm process according to the above-mentioned embodiment inhibits the alarm output when the emotion flag indicates that the face expresses the specific emotion. The doze alarm process may inhibit the drowsiness level determination process from being performed. In this case, however, the drowsiness level determination process needs to be performed at least after the emotion expression determination process.

According to the above-mentioned embodiment, the feature distance calculation process, the wakefulness reference value calculation process, the open eye reference value calculation process, the characteristic opening degree value calculation process, and the characteristic opening degree value calculation process calculate the feature distances L1, L2, L3, and L4 as many as the first or second prescriptive count hereafter referred to as a prescriptive count. When the second or later determination at S1350 or the like yields an affirmative result, the process calculates the opening degree value L and the closed eye value L also referred to simply as indexes. Thereafter, the process extracts the indexes stored in the RAM 10b as many as the prescriptive count in a chronological order starting from the one that is most recently stored in the RAM 10b. That is, the processes use the newly calculated and updated indexes as many as the prescriptive count to calculate the representative feature distance, the representative opening degree value, the representative open eye value, the characteristic opening degree value, and the characteristic feature distance can be referred to as a representative feature distance and the like. The representative distance may be calculated after updating all the indexes as many as the prescriptive count so as not to duplicate the index used for the representative distance.

It may further be desirable to provide a setting of the first counter to the initial value and deleting the representative distance and the like when a negative result is derived from the determination at S1350 of the feature distance calculation process, at S1450 of the wakefulness reference value calculation process, at S1650 of the closed eye reference value calculation process, at S2150 of the characteristic opening degree value calculation process, and at S2250 of the characteristic feature distance calculation process.

The emotion expression determination process according to the above-mentioned embodiment performs the compatible t-test using the characteristic feature distances L1$d$, L2$d$, L3$d$, and L4$d$ and the representative feature distances L1$a$, L2$a$, L3$a$, and L4$a$. According to a result, the emotion expression determination process determines whether the face expresses the specific emotion. However, the invention is not limited to such a determination method. For example, the feature distance calculation process calculates the representative feature distance. Using the representative distance as a threshold value, the emotion expression determination process may determine whether the characteristic feature distance is greater than or equal to the threshold value. In such a manner, the emotion expression determination process may determine whether the face expresses the specific emotion.

The threshold value is not limited to the representative feature distance. A frequency distribution is found at S1360 of the feature distance calculation process. A standard deviation or a mode value may be calculated from the frequency distribution and may be used as the threshold value.

The drowsiness level determination process according to the above-mentioned embodiment estimates a wakefulness degree based on an increase or decrease in the opening degree value. The invention is not limited to such an estimation method. As described by the applicant in JP-B No. 036386/2007, for example, a wakefulness degree may be estimated using special indexes that represent degrees of a slacked mouth, a raised eyebrow, and a tilted head.

In such a case, the wakefulness degree calculation apparatus is constructed so that the drowsiness level determination process can estimate wakefulness degrees according to both the opening degree value and the special index. In particular, the drowsiness level determination process preferably estimates a wakefulness degree based on the eye's opening degree when the specific emotion is not assumed to be expressed according to the emotion expression determination process. The drowsiness level determination process preferably estimates a wakefulness degree based on the special index when the specific emotion is assumed to be expressed.

In such a manner, the drowsiness alarm system changes indexes for estimating a wakefulness degree depending on whether the specific emotion is expressed. Such system can reduce the possibility of incorrectly issuing an alarm according to the wakefulness degree assumed to be low simply because a specific emotion is expressed. In addition, the system can issue an alarm when an occupant is more likely to actually feel drowsy.

According to the above-mentioned embodiment, the first prescriptive distance LL1 represents a distance between the inner corner of eye and the inner end of eyebrow. It may represent a distance between inner ends of both eyebrows. That is, contraction of the corrugator muscle can be estimated even though the first feature distance L1 is based on a distance between the inner ends of eyebrows.

The second feature distance L2 according to the above-mentioned embodiment is based on the second prescriptive distance LL2, such as a distance between the upper eyelid top and an intersection between the reference line and a perpendicular line from the upper eyelid top. In addition, the opening degree value L may be used. That is, the levator palpebrae superioris can be assumed to contract when the opening degree value becomes larger than the awaked state.

The third feature distance L3 or the fourth feature distance L4 according to the above-mentioned embodiment is based on a distance between the inner corner of eye and the mouth corner. There may be another feature distance, such as a fifth feature distance L5, based on a distance between the mouth corner and the tragus point. That is, contraction of the greater zygomatic muscle can be also estimated by using a distance between the mouth corner and the tragus point.

In such a case, equation (7) is used to calculate the fifth feature distance L5.

$$L5 = \frac{\sqrt{(x9-x8)^2 + (y9-y8)^2}}{\sqrt{(x1-x2)^2 + (y1-y2)^2}} \quad (7)$$

The above-mentioned embodiment calculates the eye opening degree and the feature distance for the left and right parts of the face independently of each other. In some embodiments however, it may be advisable to calculate the eye opening degree and the feature distance for only one of the left and right parts of the face.

The feature distance and the opening degree value according to the above-mentioned embodiment are found by dividing the prescriptive distance and the distance between the upper eyelid top and the lower eyelid bottom by the distance between the inner corners of eyes. However in some embodiment, the feature distance or the opening degree value may not be divided by the distance between the inner corners of eyes. The prescriptive distance and the distance between the upper eyelid top and the lower eyelid bottom may be directly used to determine whether the face expresses the emotion, or to estimate a wakefulness degree.

Further, any index may be used when the feature distance or the opening degree value can be used for estimating a change in the eye opening degree or contraction of face muscles. For example, a possible index may be an angle formed by a first reference line connecting the inner corner of eye with the outer corner of eye and a line connecting the inner corner of eye or outer corner of eye with each feature point.

The above-mentioned embodiment calculates a feature distance based on a captured image to estimate the contraction of facial muscles. Alternatively, the muscle contraction may be detected directly from a myogenic potential such as through the direct attachment of a probe, sensor or the like to the face of the driver.

The drowsiness alarm system 1 according to the above-mentioned embodiment may be provided with a light source for applying light to the face of the driver. The light source preferably emits light in a near-infrared region. The camera 20 needs to be equipped with a filter for eliminating wavelengths other than the near-infrared region.

The cool air supply apparatus 21 according to the above-mentioned embodiment is provided in the head rest. Alternatively, the cool air supply apparatus 21 may be provided elsewhere. The cool air supply apparatus 21 may be provided, for example, anywhere when it can apply cool air to the driver so as to improve the wakefulness degree.

The above-mentioned embodiment assumes a vehicle driver to be an object of estimating the wakefulness degree and detecting the specific emotion that may be expressed. However, alternatively, the object may be an occupant other than the driver in a vehicle.

What is claimed is:

1. A drowsiness alarm apparatus comprising:
   an image acquisition means for capturing facial image data associated with a face of an occupant in a vehicle;
   a wakefulness estimating means generating an estimated wakefulness degree indicating a wakefulness degree of the occupant based on one of a first index estimated by a first index estimation means and a second index different from the first index estimated by a second index estimation means,
   wherein, based on the captured facial image data, the first index estimation means estimates the first index predetermined to estimate the wakefulness degree of the occupant and second index estimation means estimates the second index predetermined to estimate the wakefulness degree of the occupant;
   an emotion determination means for determining a specific one of a plurality of facially expressed emotions based on a change in the first estimated index for the specific one the specific one having a characteristic similar to that of a decrease in the wakefulness degree, and determining, based on a predetermined emotion index associated with associated with the captured facial image; and
   a switchover means for switching between generating the estimated wakefulness degree based on the first estimated index when the emotion determination means determines no expression of the specific one, generating the estimated wakefulness degree based on the second estimated index when the emotion determination means determines that the specific one is expressed.

2. A drowsiness alarm apparatus comprising:
   an image acquisition means for capturing facial image data associated with a face of an occupant in a vehicle;
   a wakefulness estimating means for generating an estimated wakefulness degree indicating a wakefulness degree of the occupant based on a predetermined estimation index;
   an emotion determination means for determining the presence of a specific one of a plurality of facially expressed emotions based on a change in the estimation index, the specific one having a characteristic similar to that of a decrease in the wakefulness degree, and the presence determined based on a predetermined emotion index associated with the captured facial image; and
   an inhibition means for inhibiting an alarm issued based on the estimated wakefulness degree when the emotion determination means determines that the specific one of the plurality of facially expressed emotions is expressed,
   wherein the emotion determination means includes a feature distance calculation means for calculating one of a feature angle and a feature distance associated with one or more pairs of feature points, each of the one or more pairs varying in association with a specific muscle capable of having a contraction state based on one of an expression of the specific one of a plurality of facially expressed emotions and a decrease in the wakefulness degree; and
   wherein the predetermined emotion index includes the one of the feature angle and the feature distance calculated by the feature distance calculation means.

3. The drowsiness alarm apparatus of claim 1,
   wherein the emotion determination means includes a feature distance calculation means for calculating one of a feature angle and a feature distance associated with one or more pairs of feature points, each of the one or more pairs varying in association with a specific muscle capable of having a contraction state based on one of an expression of the specific one of a plurality of facially expressed emotions and a decrease in the wakefulness degree; and
   wherein the second estimated index includes the one of the feature angle and the feature distance calculated by the feature distance calculation means.

4. The drowsiness alarm apparatus of claim 2, wherein the specific muscle includes a corrugator muscle.

5. The drowsiness alarm apparatus of claim 3, wherein the specific muscle includes a corrugator muscle.

6. The drowsiness alarm apparatus of claim 4, wherein the one or more pairs of feature points includes at least one of a pair of an inner end of a left eyebrow and an inner corner of a right eye and a pair of an inner end of a right eyebrow and an inner corner of a left eye.

7. The drowsiness alarm apparatus of claim 5, wherein the one or more pairs of feature points includes at least one of a pair of an inner end of a left eyebrow and an inner corner of a right eye and a pair of an inner end of a right eyebrow and an inner corner of a left eye.

8. The drowsiness alarm apparatus of claim 2, wherein the specific muscle includes levatora palpebrae superioris.

9. The drowsiness alarm apparatus of claim 8, wherein the one or more pairs of feature points includes an upper eyelid top, an inner corner of eye, and an outer corner of eye nearest to a parietal region of an upper eyelid.

10. The drowsiness alarm apparatus of claim 2, wherein the specific muscle includes one of a greater zygomatic muscle and a risorius muscle.

11. The drowsiness alarm apparatus of claim 10, wherein the one or more pairs of feature points includes an inner corner of eye and a mouth corner.

12. The drowsiness alarm apparatus of claim 10, wherein the one or more pairs of feature points includes a mouth corner and a tragus point.

13. The drowsiness alarm apparatus of claim 2,
wherein the feature distance calculation means calculates the one of the feature angle and the feature distance associated with the one or more pairs of feature points independently for a left and a right part of the face of the occupant; and
wherein the emotion determination means assigns the emotion index based on the one of the feature angle and the feature distance associated with one of the left and the right side based a large variation therebetween.

14. The drowsiness alarm apparatus of claim 3,
wherein the feature distance calculation means calculates the one of the feature angle and the feature distance associated with the one or more pairs of feature points independently for a left and a right part of the face of the occupant; and
wherein the emotion determination means assigns the second estimated index based on the one of the feature angle and the feature distance associated with one of the left and the right side based a large variation therebetween.

15. The drowsiness alarm apparatus of claim 3, wherein the one or more pairs of feature points includes inner ends of left and right eyebrows.

16. A drowsiness alarm apparatus comprising:
an image acquisition means for capturing an image including a face of an occupant in a vehicle;
a wakefulness estimate means for detecting an estimated index predetermined as an index for estimating a wakefulness degree of the occupant based on the captured image and generating an estimated wakefulness degree indicating a wakefulness degree of the occupant based on the detected estimated index;
an alarm means for performing an alarm process for issuing an alarm when an estimated wakefulness degree generated by wakefulness estimate means is smaller than a predetermined prescriptive wakefulness degree;
a specific emotion determination means for determining a specific emotion out of facial emotions based on a change in the estimated index for the specific emotion indicating a tendency similar to a decrease in the wakefulness degree and determining whether a face in the captured image expresses the specific emotion based on a predetermined emotion index extracted from the captured image; and
an inhibition means for inhibiting the alarm means from performing an alarm process when the specific emotion determination means determines that a specific emotion is expressed,
wherein the specific emotion determination means includes a feature distance calculation means that uses a specific facial muscle showing different contraction states depending on expression of the specific emotion and a decrease in the wakefulness degree, extracts from the captured image one or more pairs of feature points defined to vary a distance therebetween in connection with the specific facial muscle, and calculates a feature angle between extracted feature points or a feature distance between the feature points; and
wherein the specific emotion determination means uses one of a feature angle and a feature distance calculated by the feature distance calculation means as the emotion index.

17. The drowsiness alarm apparatus of claim 16, wherein the specific muscle includes one of an levator palpebrae superioris, a corrugator muscle, a greater zygomatic muscle and a risorius muscle.

18. The drowsiness alarm apparatus of claim 16, wherein the feature points include at least one of a first pair including an inner end of a left eyebrow and an inner corner of a right eye, and a second pair including an inner end of a right eyebrow and an inner corner of a left eye.

19. The drowsiness alarm apparatus of claim 16, wherein the feature points include an upper eyelid top, an inner corner of an eye, and an outer corner of an eye nearest to a parietal region of an upper eyelid, a mouth corner, a tragus point, and inner ends of left and right eyebrows.

20. The drowsiness alarm apparatus of claim 16,
wherein the feature distance calculation means extracts the feature points and calculates the feature distance for left and right parts of the face independently of each other; and
wherein the specific emotion determination means assigns the emotion index to one of left and right feature distances independently calculated by the feature distance calculation means based on the feature distance indicating a large variation.

21. An article of manufacture comprising a computer readable medium and instructions carried on the computer readable medium, the instructions, when read by a computer for causing the computer to function as means included in the drowsiness alarm apparatus of claim 1.

* * * * *